United States Patent [19]

Bruschi

Best Available Copy

[11] E Re. 30,267

[45] Reissued May 6, 1980

[54] MULTILAYER ANALYTICAL ELEMENT

[75] Inventor: Barbara J. Bruschi, Olathe, Kans.

[73] Assignee: Eastman Kodak Company, Rochester, N.Y.

[21] Appl. No.: 907,362

[22] Filed: May 18, 1978

Related U.S. Patent Documents

Reissue of:

[64] Patent No.: 4,066,403
Issued: Jan. 3, 1978
Appl. No.: 688,446
Filed: May 20, 1976

U.S. Applications:

[63] Continuation-in-part of Ser. No. 588,755, Jun. 20, 1975, abandoned.

[51] Int. Cl.[2] ..... G01N 33/16; G01N 31/22

[52] U.S. Cl. ..... 23/230 B; 435/12; 422/56; 422/57; 422/58

[58] Field of Search ..... 422/55-58; 23/230 B, 230 R; 195/103.5 R, 103.5 B

[56] References Cited

U.S. PATENT DOCUMENTS

| | | | |
|---|---|---|---|
| 3,011,874 | 12/1961 | Deutsch | 422/57 |
| 3,249,513 | 5/1966 | Babson | 23/253 TP X |
| 3,630,957 | 12/1971 | Rey et al. | 252/408 |
| 3,699,003 | 10/1972 | Kronish et al. | 23/253 TP X |
| 3,822,189 | 7/1974 | Tornmarck | 195/103.5 R |
| 3,838,033 | 9/1974 | Mindt et al. | 204/195 B |
| 3,926,734 | 12/1975 | Gray et al. | 195/103.5 R |
| 3,992,158 | 11/1976 | Przybylovicz et al. | 422/58 |

FOREIGN PATENT DOCUMENTS

| | | | |
|---|---|---|---|
| 50-93494 | 7/1975 | Japan . | |
| 1287785 | 9/1972 | United Kingdom | 23/253 TP |

*Primary Examiner*—Michael S. Marcus
*Attorney, Agent, or Firm*—Dana M. Schmidt

[57] ABSTRACT

An analytical element for assay of complex fluids, such as blood, the element comprising two reagents and a barrier composition separating the reagents. Such an element is particularly useful in the analysis of blood for urea nitrogen and cholesterol content.

52 Claims, 5 Drawing Figures

MULTILAYER ANALYTICAL ELEMENT

Matter enclosed in heavy brackets [ ] appears in the original patent but forms no part of this reissue specification; matter printed in italics indicates the additions made by reissue.

RELATED APPLICATIONS

[This application is a continuation-in-part application of Ser. No. 588,755 filed on June 20, 1975 and now abandoned.]

*This application is a reissue application for U.S. Pat. No. 4,066,403 issued on Jan. 3, 1978 on U.S. Ser. No. 688,446 filed on May 20, 1976, a continuation-in-part application of Ser. No. 588,755, June 20, 1975, abandoned.*

BACKGROUND OF THE INVENTION

1. Field of the Invention

This invention relates to analytical chemistry and in particular to an improved multilayer analytical element for analysis of body fluids for specific components, and more specifically to an element useful in the analysis of blood serum for blood urea nitrogen (BUN) content.

2. State of the Prior Art

In recent years, a number of automated systems for carrying out chemical analyses of fluid samples have been developed; and these have proven particularly advantageous for use in clinical laboratories, especially in the quantitative analysis of blood. Systems based on continuous flow analysis in which sample, diluents and test reagents are mixed together and transported through the analyzer are very widely utilized. However, these continuous analyzers, such as, for example, the analyzer illustrated in U.S. Pat. No. 2,797,149, are complex and expensive, require skilled operators, necessitate considerable expenditure of time and effort in repetitive cleaning operations, and do not permit the use of very small quantities of sample, such as are used in microanalytical techniques. In an effort to overcome these disadvantages, automated chemical analyzers have been proposed which utilize a continuous analytical tape on which the sample to be analyzed is deposited and which effect quantitative analysis by means of spectrophotometric measurement of color-forming reactions between constituents of the sample to be analyzed and test reagents applied to or carried by the tape. Analyzers of this type are described in detail in many patents, for example, in British Pat. No. 1,049,364 and in U.S. Pat. Nos. 3,036,893 and 3,526,480.

The analyzers utilizing continuous analytical tapes are inherently much simpler than continuous flow analyzers. However, analytical tape analyzers such as are described in the aforesaid patents suffer from many significant disadvantages which have hindered their commercial development. Thus, where the tape does not incorporate the test reagents within itself and is merely utilized as a means of transporting the sample to be analyzed through the system, as in certain embodiments of British Pat. No. 1,049,364, provision must be made for separate application of sample and test reagents to the tape at the right time and in the right amounts. The use of separate tapes to accomplish various functions, such as sample filtering, and reaction of the sample with the test reagents, as in U.S. Pat. No. 3,036,893 and in certain other embodiments of British Pat. No. 1,049,364, adds greatly to the complexity of the system so that the inherent simplicity of the continuous tape method of analysis is not fully realized. Use of analytical tapes of a complex nature which are difficult and expensive to manufacture, such as are described in U.S. Pat. No. 3,526,480 is, of course, also a serious hindrance to achieving a commercially practical system.

Other "dry" systems to perform quantitative or semiquantitative determination of blood components have also been devised. These include primarily the incorporation of reagents into bibulous carrier materials such as paper or porous hydrophilic polymeric layers which may or may not also include overcoats of dialyzing materials to filter out undesirable blood components such as red cells. Specifically, in the case of blood urea nitrogen (hereafter BUN), urease is imbibed into a bibulous carrier overcoated with a dialyzing membrane (U.S. Pat. Nos. 3,145,086; 3,249,513; 3,395,082; and Brit. Pat. No. 1,287,785). According to the teachings of these patents, the ammonia released by the reaction of urea with oxygen in the presence of urease initiates a color change in an imbibed pH indicator. However, the usefulness of these systems is adversely affected by the presence of other basic materials which falsely affect the indicator. The dialyzing membrane, if used, is only a macrofilter positioned as the outermost layer. Barrier bands are disclosed as options, but these are used to divide the test strip lengthwise into regions of different sensitivity, and these barriers do not function to permit selective migration into interior layers.

The disclosure of U.S. Pat. No. 3,011,874 indicates that other barrier bands have been considered for BUN test elements heretofore. However, as disclosed in this patent, the barrier is a barrier to all substances, the ammonia being released by a gas release band for atmospheric diffusion to the indicator band in a closed container.

Still other systems have been developed based upon the urease reaction, but these have been largely confined to liquid reactions. Patents representative of this approach include U.S. Pat. Nos. 3,409,508 and 3,485,723. Still other patents which are relevant only to the general background of BUN analysis include U.S. Pat. Nos. 3,718,433; 3,655,516; 3,567,374; 3,511,611, and 3,531,254.

U.S. Pat. No. 3,723,064 provides a layered test element useful in clinical analysis, wherein two reagent layers are separated by intermediate layers. One of these layers may have chemical traps of varying concentration, which are specific to the end product being tested for. Barriers may be provided for the intermediate layers in the form of a plurality of vertically extending barrier compositions such as cellulose acetate to control concentration gradients flowing through the intermediate layer. The barriers do not function to intercept interfering or undesired components as they flow from one reagent layer to the other in their normal direction of flow. Furthermore, they vary in concentration within the sample intercept area of the element.

U.S. Pat. No. 3,901,657, describes a filter paper layer as a physical separation between a reagent-containing layer and an indicator layer. The entire liquid sample and its components are permitted to pass through the filter paper. No suggestion is made that the paper layer should selectively pass only a portion of an applied sample or a decomposition product of the analytical reaction.

A recent approach to the problem of blood analysis is disclosed in commonly-owned U.S. application Ser.

No. 538,072, filed Jan. 2, 1975, entitled "Integral Analytical Element," by Edwin P. Przybylowicz et al., now U.S. Pat. No. 3,992,158. In this approach, an element comprising a reagent layer, an isotropically porous spreading layer, and additional layers which may include a dialysis layer, a filtering layer, a reflecting layer, or a combination of any of these is used to generate a detectable change, such as a quantifiable shift in energy absorption or transmission in response to the presence of an analyte in a sample being tested. The reagent layer is in fluid contact with the spreading layer, as are the additional layers, so that the component being analyzed or a precursor thereof or reaction product thereof will reach the reagent layer. The suggested filter or dialysis layer(s) are described as functioning to exclude passage of filterable materials present in the sample, and to pass sample components not trapped in the filter layer. Such filter or dialysis layers are not described as being specifically concerned with preferential passage of a decomposition product produced directly or indirectly by materials contained in a reagent layer positioned ahead of the filter in the normal flow of the fluid under study, to the exclusion of possibly interfering substances.

Enzyme electrodes using semipermeable membranes selectively permeable to a material of choice have been used in conjunction with an enzyme layer and an electrode means for potentiometrically registering a decomposition product produced by the enzyme, such as, ammonia produced from urea in the presence of urease. Such devices are disclosed, for example, in U.S. Pat. No. 3,838,033 and U.S. Pat. No. 3,896,008.

OBJECTS OF THE INVENTION

It is an object of the invention to provide an improved "dry" analytical element for complex fluid analysis for an analyte, which is protected against the intrusion of undesirable alternate reactive materials which could falsify the reading.

Yet another object of the invention is to provide such an element which provides a quantitative analysis of blood components such as urea nitrogen.

Other objects and advantages will become apparent upon reference to the following Summary of the Invention and Discussion of the Preferred Embodiments, when read in light of the attached drawings.

SUMMARY OF THE INVENTION

According to the present invention, there is provided an improved integral analytical element for the assay of an analyte in a liquid sample applied thereto.

According to one aspect of the invention, there is provided an improvement of an integral element useful in the analysis of a fluid sample for a predetermined analyte, the element including a reagent capable of interacting in the presence of the analyte to produce a decomposition product; and a reagent capable of interacting with the decomposition product or an intermediate to provide a detectable change; the improvement comprising a barrier composition separating the reagents, the barrier composition being substantially uniformly permeable to the decomposition product and substantially impermeable to interferants. Such an element has particular utility in the analysis of BUN, wherein the enzyme urease converts urea to $NH_3$.

According to another aspect of the invention, there is provided an integral, multilayered element useful in the analysis of a fluid sample for an analyte, the element including, in superposed relationship (1) a first layer which includes a sample intercept area, and reagent in that area capable of interacting with the analyte to produce a decomposition product; and (2) a second layer which includes at least one reagent capable of interacting with the decomposition product or an intermediate to form a detectable change; the improvement comprising a barrier composition separating the first and second layer reagents and having a sample intercept area that is at least coextensive with the sample intercept area of the first layer, the barrier composition within its sample intercept area being uniformly permeable to the decomposition product and impermeable to interferants.

DESCRIPTION OF THE PREFERRED EMBODIMENTS

Figure 1:
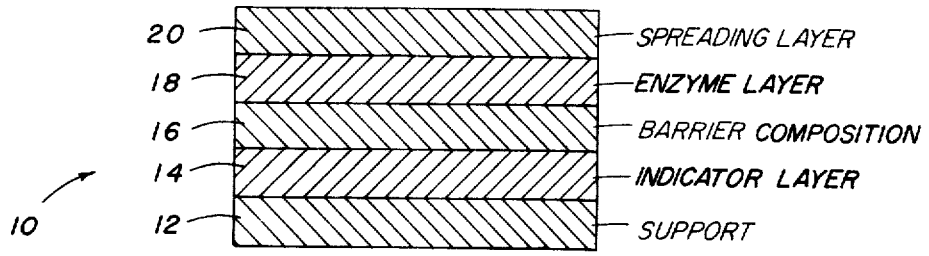
FIGS. 1-5 are enlarged sectional views of elements constructed in accordance with the invention, each view illustrating an alternate embodiment.

In an analytical element relying upon a reaction between a reagent and a component of a liquid sample, the tendency of the reagent to undergo undesirable reactions is a problem. The reagents of the element desirably produce with the analyte a prescribed sequence. However, by-products of that sequence may produce a detectable change by interacting with any of the reagents, or components of the liquid sample being tested other than the analyte of choice may react to cause a detectable change. If this in fact occurs, error is introduced into the detection. It is such reaction by-products or other liquid sample components that are hereinafter called "interferants," and which are to be excluded from the reagent which causes the detectable change, in order to achieve quantitative results. According to the instant invention, there is provided a novel integral analytical element which solves this problem by excluding the interferants from the indicator reagent. The analytical element of the invention is simple in structure, easily manufactured at reasonable cost, and adapted to carry out the analysis in a simple and effective manner. This analytical element can be utilized in the form of a continuous strip or tape, or in other forms, such as sheets or short strips or in the form of small sections or chips which may or may not be mounted in aperture cards or other holding devices. All such forms of the element are considered to be equivalent and within the scope of the present invention. Furthermore, although the preferred form of such element is a multilayered element, the invention is not so limited. Rather, it is directed to any element providing for the separation of the two reagents as hereinafter defined and described, by a barrier composition having the desired selective permeability during the time period needed for any test of choice. As used herein, "substantially permeable" or "permeable" means that substantially all of the decomposition product presented to the barrier composition actually passes through it within the time of the test.

Quantitative analysis for the particular constituents of the sample, for example, an analysis for urea nitrogen in blood serum, is readily accomplished by use of conventional spectrophotometers or other techniques capable of measuring in a rapid manner and with high degrees of accuracy the amount of radiant energy-detectable product produced in the assay reaction.

As used herein, "radiant energy-detectable" product or species refers to a product or species which, by either the formation or loss of color, fluorescence, or other characteristics, alters the radiant energy transmission or reflection characteristics of the element. As used herein, "decomposition" includes but is not limited to dissociation, dehydration, hydrolysis, and the like. "Intermediate" means a substance produced by reaction of the product of a decomposition with yet another substance or substances, such as a reagent, incorporated into the element.

As used herein, "reagent" means a material that is interactive with an analyte, a precursor of an analyte, a decomposition product or an intermediate. Such interaction is meant to refer to chemical reactivity, catalytic activity as in the formation of an enzyme-substrate complex, or any other form of chemical or physical interaction that can result in the ultimate production within the element, such as in the layer containing the reagent, of a change that is detectable, by suitable measurement of radiant energy, usually in the form of light energy. Although the disclosure hereinafter is directed to a particularly useful combination wherein the reagents are at least one enzyme which produces the decomposition product, and at least one indicator which responds to the decomposition product to register the detectable change, any other reagents can be used provided they come within the scope of the above definition.

The element preferably is laminar in construction, so that when observed as a transverse cross-section, the layers are seen as superposed. Such a construction permits a drop of the sample to diffuse, under the influence of gravity, capillary effects, wicking, etc., from the outmost layer into one or more interior layers.

In use, a sample of the fluid to be analyzed is applied to the exterior surface of the element. Each layer of the element has a sample intercept area. As used herein with respect to a layer, the term "sample intercept area" refers to the entire surface area intended for wetting by an applied sample, or any decomposition product of a component of the sample, in its normal movement through the element, at any given cross-section of the element transverse to fluid flow. Preferably, there is a uniform distribution of the components within each sample intercept area of each layer so as to provide a uniform result within that layer.

Such compositional uniformity is important to obtaining quantitative determinations when the result produced in the element is measured by radiometric apparatus such as a reflectometer. As used herein, "uniform" when used to describe the composition of layers means that any given volume of such layer will contain a substantially identical concentration of material as any other similar volume. Preferably, such uniformity is achieved by forming the layer in question with a uniform thickness and a uniform amount of reagent or barrier composition throughout the thickness.

It is preferred that the sample intercept area of the barrier composition in contact with the reagent layer previously encountered by the fluid, be at least substantially coextensive with that of such reagent layer previously encountered, to insure that undesired materials are excluded from the sample intercept area of the indicator layer during the time of the test. Of course, the sample intercept area of the barrier composition can also be considerably greater than such coextensive size.

In one preferred embodiment, the element thus includes a support, layers overcoated or otherwise integrally formed on one side of the support and including at least an indicator, a barrier composition, a layer containing an enzyme, and superposed on the other layers, a spreading layer which spreads and meters sample applied to the element. The enzyme layer can incorporate one or more enzymes, depending on the assays to be performed.

The drawings further illustrate the invention. Each layer depicted is shown for its entire sample intercept area. Thus, each layer's intercept area is coextensive with that of the adjacent layers. It will be appreciated that each layer can also be extended beyond the sample intercept area shown, and that such extensions do not require the presence of the reagents or barrier composition inasmuch as the fluid sample, analyte, and/or decomposition product(s) do not contact or penetrate into such extensions.

FIG. 1 illustrates one embodiment, in which element 10 comprises a support 12, an indicator layer 14, a barrier composition 16, an enzyme layer 18, and a spreading layer 20 defining the surface of the elements to which the sample is applied. Layer 20 also provides other functions as desired, such as filtration and/or a reflection, as described in more detail hereinafter, and is separate and distinct from layer 18.

FIGS. 2 through 5 illustrate alternate embodiments wherein the layers have been variously recombined. Parts similar to those previously described bear the same reference numeral to which the distinguishing suffixes "a" through "d," respectively, have been attached.

Figure 2:
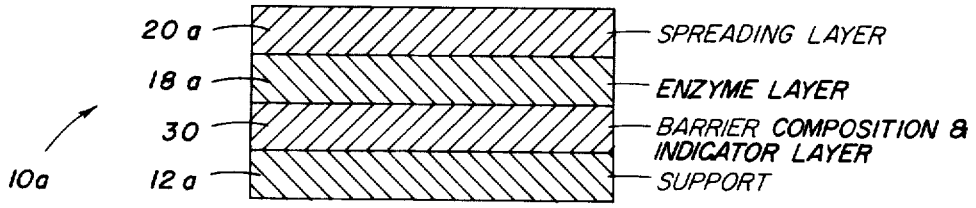

Thus, in FIG. 2 the element 10a comprises a support 12a, a spreading layer 20a, and an enzyme layer 18a as before. However, the barrier composition incorporates the indicator to form a combined layer 30, rather than being disposed as in the previous embodiment as a fourth layer between the two layers containing the enzyme and the indicator.

Figure 3:
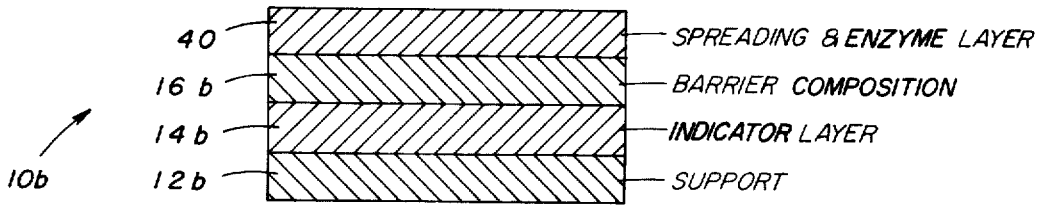

In FIG. 3, the element 10b comprises a support 12b, an indicator layer 14b, and a barrier composition 16b as in FIG. 1. However, the enzyme layer 18a has been incorporated into the spreading layer to form a combined layer 40.

Figure 4:
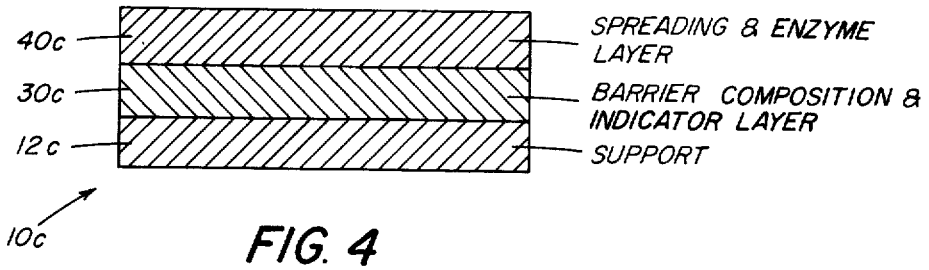

In FIG. 4, the element 10c comprises a support 12c, and only two other layers 30c and 40c, which comprise the barrier composition-indicator layer of FIG. 2 and the spreading-enzyme layer of FIG. 3, respectively.

Figure 5:
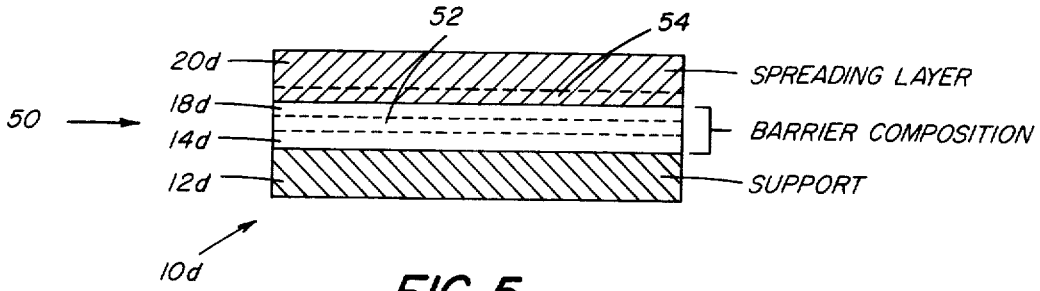

In FIG. 5, the element 10d comprises a support 12d, and spreading layer 20d as in FIG. 1, and a middle layer 50. The middle layer comprises the barrier composition throughout, but the two surface portions of layer 50 include additional ingredients as follows: a portion 14d contiguous with layer 12d that includes the indicator for detecting the decomposition product, and a portion 18d contiguous with the spreading layer 20d that includes the enzyme. The middle portion 52 which is free of both the enzyme and the indicator is optional as long as there is no overlap of portions 14d and 18d. In this embodiment, the barrier composition comprises the binder for the enzyme and the indicator. It will be appreciated, of course, that this embodiment is suitable only for those tests in which the analyte, as well as the decomposition product produced therefrom, is capable of penetrating the barrier composition. If the analyte will not so penetrate the latter, a portion of the enzyme must be included in layer 20d, shown in FIG. 5 as portion 54.

As is apparent from the preceding discussion, whatever embodiment is used, certain functions must be provided: the sample applied to the element is spread uniformly in the element, preferably by means of a spreading layer; the analyte of choice is decomposed, preferably by an enzyme; the decomposition product selectively permeates to the indicator, preferably via a barrier composition; and an indication of the amount of decomposition product is generated, representing the amount of analyte present in the applied sample. Preferably the indicator is in the form of a dye precursor or bleachable dye. Each of those functions and their preferred means will be considered separately in detail in the sequence of their occurrence.

THE SPREADING LAYER

A sample applied to the element first is distributed uniformly, preferably by one or more layers which perform this function, so as to provide a uniform apparent concentration at the surface of the spreading layer in fluid contact with adjacent layer(s). The sample spreading layer in the multilayer analytical element is generally the layer upon which the liquid sample to be analyzed, such as a sample of whole blood or blood serum, is deposited. Typically, the sample can be applied to the sample spreading layer in drop form. As used herein, "fluid contact" means contact which permits a fluid, or one or more of its components, whether liquid or gaseous, to pass or be transported between the layers.

As disclosed in the aforesaid Przybylowicz et al application, a sample spreading layer can be provided which is capable of distributing or metering within the layer a substance or substances including at least a component of a liquid sample applied to the element, to provide, at any given time, a uniform concentration of such substance at the surface of the spreading layer facing, i.e. closer to, the enzyme layer. The applied sample need not be confined. As will be appreciated, such concentration, although instantaneously uniform, can change over a period of time without deleterious effects. Concentration gradients may even exist in the layer from top to bottom. In the discussion of the various preferred embodiments, reference to isotropic porosity identifies the fact of substantial porosity in all directions within the spreading layer. It will be understood that the degree of such porosity may be variable, if necessary or desirable, for example regarding pore size, percentage of void volume or otherwise. It shall be understood that the term isotropic porosity (or isotropically porous) as used herein should not be confused with the terms isoporous or ionotropic, often used with reference to filter membranes to signify those membranes having pores that are continuous between membrane surfaces. Likewise, isotropic porosity should not be confused with the term isotropic, used in contradistinction to the term anisotropic, which signifies filter membranes having a thin "skin" along at least one surface of the membrane. See for example, Membrane Science and Technology, James Flinn ed. Plenum Press, New York (1970).

As will be appreciated, the extent of spreading is dependent in part on the volume of liquid to be spread. However, it should be emphasized that the uniform concentration obtained with spreading is substantially independent of liquid sample volume and will occur with varying degrees of spreading. As a result, elements of this invention do not require precise sample application techniques. However, a particular liquid sample volume may be desirable for reasons of preferred spread times or the like. Because the elements of this invention are able to produce quantitative results using very small sample volumes than can be entirely taken up within a conveniently sized region of the spreading layer (e.g. 1 square centimeter), there is no need to remove excess moisture from the element after application of a liquid sample. Further, because spreading occurs in the spreading layer and the spread substance is provided to the enzyme layer and without apparent substantial lateral hydrostatic pressure, there is not the "ringing" problem often seen with prior analytical elements when soluble reagents were used.

The spreading layer need only produce a uniform concentration of spread substance per unit area at its surface facing the enzyme layer with which the spreading layer is in fluid contact. A convenient method of determining whether a particular layer can be suitable for spreading purposes includes densitometric or other analytical techniques, as by scanning the appropriate surface or reagent layer or other associated layer to determine the apparent concentration of spread substance or of any reaction product based on the concentration of spread substance. The following test, disclosed in the aforementioned Przybylowicz and Millikan application, Ser. No. 538,072, is intended only as an example and the selection of materials or test parameters does not indicate, expressly or by implication, that other materials or parameters may not be suitable for similar purposes.

In conducting such a test one can apply to a transparent photographic film support material, such as subbed poly(ethylene terephthalate), a transparent gelatin layer at a gelatin coverage of about 200 mg/dm$^2$. The gelatin may vary in hardness, but for testing purposes a layer of gelatin hardened to swell the layer thickness by about 300% when immersed for 5 minutes in 22° C. water is suitable. When dry, the gelatin layer will have a thickness of about 30 microns. The layer to be evaluated for spreading purposes can be applied over the gelatin layer, such as by coating from solution or dispersion. A dry thickness of from about 100 to about 200 microns is convenient for this test layer. After drying the layers, a sample of test solution or dispersion can be applied to the surface of the spreading layer under evaluation, preferably in a small quantity so that not all portions of the layer are wetted by the applied sample, but desirably sufficient to create a wetted region that can include a circular area of about 8–10 millimeters in diameter. The selection of a test solution or dispersion is a matter of choice and will depend in part on the type of sample or analyte to which the layer will be exposed under conditions of actual usage. For low molecular weight materials, aqueous dye solutions can be used. A 0.0005 weight percent solution of Solatine Pink® is acceptable. For higher molecular weight materials such as proteins, an aqueous dispersion of bovine albumin dyed with Solatine Pink® can be used. After applying the liquid sample to the layer under evaluation and allowing the liquid sample to disappear from the surface of and be taken up into the layer, the test element can be turned over and the bottom surface of the proposed spreading layer can be viewed through the transparent support material and gelatin layer. If, prior to substantial evaporation of solvent or dispersion medium, the colored spot is of a substantially uniform color density when scanned by a densitometer having a circular aperture of about 2–3 millimeters in diameter, then spreading and the achievement of a uniform apparent concentration at the bottom surface of the test layer and/or in the gelatin layer has taken place and the test layer may be useful as a spreading layer in analytical elements of the type described herein. By "substantially uniform density" is meant a density across the spot, with the exception of its periphery, having maximum and minimum values not more than ±10–15% from the mean density. Due to edge effects, non-characteristic density gradients may arise at the spot periphery but need have no effect on the significance of an analytical result. Peripheral area can vary between spots, but it will usually not be more than about 20% of the entire spot and may be less.

Such spreading layers can be prepared using a variety of components. In a preferred form the layer is nonfibrous. In one aspect, particulate material can be used to form such layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, lead oxide, etc., are desirable. Other desirable particles are diatomaceous earth and microcrystalline colloidal materials derived from natural or synthetic polymers. Such mcirocrystalline materials are described in an article entitled, "Colloidal Macromolecular Phenomena, Part II, Novel Microcrystals of Polymers" by O. A. Battista et al published in the Journal of Applied Polymer Science, Vol. II, pages 481–498 (1967). Microcrystalline cellulose, which is commercially available from FMC Corporation under the name Avicel®, is an example of such a colloidal material which is satisfactory for use in the present invention. Spherical particles of uniform size or sizes, such as resinous or glass beads, can also be used and may be particularly desirable where uniform pores are advantageous, such as for selective filtration purposes. If a particulate material of choice is not adherent, as in the case of glass beads or the like, it can be treated to obtain particles that can adhere to each other at points of contact and thereby facilitate formation of an isotropically porous layer. As an example of suitable treatment, nonadherent particles can be coated with a thin adherent layer, such as a solution of hydrophilic colloid like gelatin or polyvinyl alcohol, and brought into mutual contact in a layer. When the colloid coating dries, the layer integrity is maintained and open spaces remain between its component particles.

As an alternative or in addition to such particulate materials, the spreading layer can be prepared using isotropically porous polymers. It is possible to prepare such polymers using techniques useful in forming "blush" polymers. "Blush" polymer layers can be formed on a substrate by dissolving a polymer in a mixture of two liquids, one of which is a lower boiling, good solvent for the polymer and the other of which is of a higher boiling point and is a non-solvent or at least a poor solvent for the polymer. Such a polymer solution is then coated on the substrate, and dried under controlled conditions. The lower boiling solvent evaporates more readily and the coating can become enriched in the liquid which is a poor solvent or non-solvent. As evaporation proceeds, under proper conditions, the polymer forms as an isotropically porous layer. Many different polymers can be used, singly or in combination, for preparing isotropically porous "blush" polymer spreading layers for use in this invention, typical examples being polycarbonates, polyamides, polyurethanes and cellulose esters such as cellulose acetate.

It can also be desirable to include within an element one or more reflective layers, optionally absorptive to detecting radiation, such as to facilitate result detection by reflection radiometry, e.g. reflection photometry or a similar technique. Such reflectance can be provided by a layer also serving, for example, as a spreading layer or it can be provided by an additional layer that may not have an additional function within the element. Pigments, such as titanium dioxide and barium sulfate, are reflective and can be used to advantage in a reflecting layer. Blush polymers can also constitute a suitable reflecting material. As can be appreciated, pigment spreading layers may be useful for this purpose as can blush polymer layers that may also be spreading layers. In one preferred aspect, blush polymer layers can also incorporate a pigment to enhance spreading and/or reflectivity. The amount of pigment that can be included in a layer together with blush polymer is highly variable, and amounts of from about 1 to about 10 parts by weight of pigment per part by weight of blush polymer are preferred, with from about 3 to about 6 parts pigment per part of blush polymer being most preferred.

Interlayer adhesion problems can be overcome without harmful effect by means of surface treatments including extremely thin application(s) of subbing materials such as are used in photographic films.

Enzymes

To cause the analyte to be decomposed to a product useful for detection, the sample is preferably distributed, by the spreading layer described above, to a suitable enzyme. The enzyme can be coated in a separate enzyme layer, or it can be incorporated in the spreading layer discussed above. The particular enzyme depends upon the assay and in the analysis of BUN to generate ammonia, a particularly useful enzyme is urease. The source of the urease appears to be of little significance.

The enzyme layer preferably comprises a binder at coverages of from about 3.0 g/m$^2$ to about 30.0 g/m$^2$, a suitable amount of enzyme, and a buffer system to maintain the pH. The enzyme generally operates efficiently only within a relatively narrow pH range. Therefore, it is generally necessary to buffer the layer containing the enzyme at some pH value within the operative pH range of the enzyme. However, this must be balanced against the pH requirements of the equilibrium conditions of the desired decomposition product. Thus, although it is possible to detect some enzymatic activity outside of this range, it is desirable to buffer the enzyme layer containing the urease to a pH between about 5 and 9.5 and preferably between about 7.5 and 9.0. Techniques for achieving this type of buffering are well known in the art and involve dissolving or dispersing the buffering agent in the dope prior to coating. Suitable buffering agents for buffering to the aforementioned pH are described in detail by Good in Biochemistry 5, 467 (1967). Particularly useful buffers include the phosphates such as potassium phosphate, the so-called Tris and Hepes buffers, and dimethyl glutarate.

The enzyme layer can also include additional compounds such as dithiothreitol, an enzyme activator, at coverages of from about 0.5 mg/m$^2$ to 5.0 mg/m$^2$ and coating aids discussed under "Preparation". The activator empirically has been found to increase the catalytic activity of the enzyme by a mechanism that is not well understood. Also, compounds can be included which will form complexes with heavy metal ions which might otherwise inhibit the activity of the enzyme.

Useful concentrations of such complexing agents range from 150 mg/m$^2$ to 500 mg/m$^2$.

In the particularly useful embodiment for the analysis of BUN, the enzyme layer thus comprises a binder such as gelatin, agarose, polyvinyl alcohol, or the like; a suitable amount of urease between about 4000 U/m$^2$ and about 50,000 U/m$^2$, and preferably between about 10,000 U/m$^2$ to about 30,000 U/m$^2$; an ethylene diamine tetracetic acid salt as metal ion complexer; and an ortho-phosphate activator.

Barrier Composition

After formation of the decomposition product by the catalytic effect of the enzyme, described above, it is an aspect of this invention to isolate the indicator, during the time of the test, from interferants, by preventing access to the indicator by such interferants. This is preferably achieved by the selectively permeable barrier composition separating the enzyme reagent from the indicator reagent. As used herein, "barrier composition separating the reagents" means a composition physically isolating one reagent from the other. Preferably, the composition is in the form of either a discrete layer between and spacing apart separate, adjacent layers containing reagents in a sample intercept area, as defined above, or a dispersal or distribution in the whole or a portion of the layer incorporating the enzyme and/or the layer incorporating the indicator. Such compositions, which form the "barrier layer," serve the function of isolating the indicator producing the radiant energy-detectable product, hereinafter described in detail, from undesired interferants. The barrier composition is not to be confused with conventional filtering layers, which are ineffective in excluding all but a limited selection of materials. The barrier composition of this invention is uniformly impermeable to interferants. As used herein, "uniformly impermeable" means impermeable or substantially impermeable during the period of the analysis in question, to the extent of excluding from the indicator to the same extent across the sample intercept area, any interferants present in or produced from the sample. The period of analysis varies depending on the analyte and the reagents used in the assay. One preferred form of the element provides such a barrier composition in the form of a layer having a sample intercept area in which the barrier composition is uniformly distributed and which is at least coextensive with the intercept area of the enzyme layer. Thus, the barrier composition can be confined to a separate layer which is contiguous with and between the layer containing the enzyme and the layer containing the indicator, or it may be dispersed throughout all or a portion of either the enzyme layer or the indicator layer. Alternatively, the enzyme and the indicator may be incorporated into opposite surface portions of a layer formed by the barrier composition, leaving an optional central portion comprising the barrier composition essentially free of either the indicator or the enzyme.

The barrier composition selected, and the amounts thereof, will depend of course on the decomposition product which is to pass therethrough. In the analysis of BUN, the composition must be impermeable, under atmospheric pressure, to liquid bases present in blood or blood serum and relatively permeable to ammonia vapor. When urease is the enzyme, the barrier composition is ideally impermeable to liquid water and thus impermeable to aqueous bases, but permeable to ammonia vapor. For this reason, at least some of the urease must be outside of the layer formed by the barrier composition. In this fashion, other bases which might react with the indicator to falsify the urea indication are excluded. The barrier composition may comprise a stratum of any thickness which permits passage of ammonia therethrough in at least one direction while simultaneously inhibiting the passage of aqueous bases, for the time alloted for completion of the test. A typical time for the test, particularly in the case of BUN analysis, is from about 5 to about 20 minutes. Particularly useful materials of this type of ammonia-permeable, water-impermeable barrier composition include cellulose acetate butyrate, having between about 10 and about 60 weight percent butyryl content and between about 5 and about 30 weight percent acetyl content, cellulose propionate valerate having between about 20 to about 50 weight percent valeryl content, poly(methylmethacrylate), and cellulose acetate acetylated to have an acetyl content above 19%, and preferably about 40%. Such a barrier composition, in passing only ammonia vapor during the time of the test for BUN, permits the desired reaction with the indicator which forms the color change while inhibiting any potentially interfering reactions.

Although some ammonia is inherently present in blood and will be detected in the form of permeated ammonia vapor, it is negligible compared to the ammonia produced from the urea and can be ignored.

The barrier composition for the analysis of BUN, whether applied as a layer separate from the indicator layer or intermixed therewith, can have a coverage ranging from about 0.10 g/m$^2$ to about 3.5 g/m$^2$, and preferably between about 0.20 g/m$^2$ and 1.0 g/m$^2$. To enhance adhesion of over-lying layers to a barrier composition formed from, for example, a cellulose ester, the surface of the barrier composition can be slightly hydrolyzed.

Indicator

The purpose of the indicator is to provide at least part of the test materials to generate a detectable change, preferably that which is reactive with the decomposition product produced in the enzyme layer.

A coating of one or more such interactive indicator materials in a hydrophilic colloid which serves as a binder or vehicle, such as de-ionized gelatin, polyvinyl alcohol, agarose, etc., is suitable. Hydrophobic binders such as cellulose acetate, cellulose acetate butyrate, ethyl cellulose, etc., permeable to a desired constituent or decomposition product of a constituent are also suitable. Alternatively, as noted above in connection with FIG. 2 the barrier composition can function as the binder without requiring any further binder for the indicator.

Particular indicators incorporated in this layer depend, of course, on the fluid component being assayed and the assay mechanism being utilized. In accordance with one aspect of this invention, wherein the element is used to detect urea via urease-catalyzed decomposition yielding ammonia, the liquid component urea and the assay mechanism, $NH_3$ production, require the indicator(s) to undergo a change in its absorption frequency in the presence of $NH_3$. Particularly useful indicators are bleachable dyes and dye precursors.

The term "dye precursor" means any composition which is capable of forming a dye by modification of molecular structure, for example, by elimination of one or more atoms such as in deprotonation, or by the combination of modified molecules with each other (autocoupling) or with a color coupler. Examples of the former include base-activatable chromogens, and examples of the latter include diazonium salts.

The particular dye precursor chosen will, of course, depend upon the decomposition product to be produced by the enzyme as described below. In the detection of BUN, the decomposition product is a base, such as ammonia. Among the base-activated chromogens, particularly useful reagents include protonated or leuco dyes, such as leuco cyanine dyes, nitro-substituted leuco dyes, and leuco phthalein dyes, which deprotonate to the dye form in the presence of a base. Representative examples include 1,2 and 1,4 substituted quinolinium salts, such as 1-methyl-2(2,4-dinitrobenzyl) quinolinium perchlorate; 1-ethyl-4(2,4-dinitro-1-naphthyl)methyl quinolinium chloride; 4(2,6-dinitro-4-chlorobenzyl)-1-propyl quinolinium ethyl sulfonate; 1-ethyl-4(2,6-dinitrobenzyl) quinolinium ethyl chloride; and 1-ethyl-4(2,6-dinitrobenzyl) quinolinium ethyl sulfonate. It will be further appreciated that similar materials having different anions are also useful, such as 1-ethyl-4(2,6-dinitrobenzyl) quinolinium chloride. Also useful are 6-(2,4-dinitrophenyl)-6H-pyrido[2,1-a]isoindolium perchlorate and the sodium salt fo phenolsulfonaphthalein.

The leuco cyanine dyes appear to form a dye in the presence of ammonia by the following route:

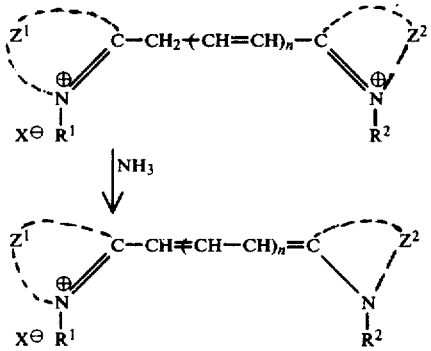

wherein n represents a positive integer of 1 to 10, $X^{\ominus}$ represents an acid anion, such as chloride, bromide, p-toluene sulfonate, methane sulfonate, ethane sulfonate, methylsulfate, ethylsulfate, perchlorate, etc.; $R^1$ and $R^2$ are the same or different and each represents hydrogen or an alkyl group, (preferably a lower alkyl containing from 1 to 4 carbon atoms), e.g., methyl, ethyl, propyl, isopropyl, butyl, hexyl, cyclohexyl, decyl, dodecyl, etc., wherein the term alkyl group is meant to include substituted alkyl groups such as substituted lower alkyl groups containing from 1 to 4 carbon atoms, such as hydroxyalkyl groups, e.g., β-hydroxyethyl, ω-hydroxybutyl, etc., alkoxyalkyl groups, e.g., β-methoxyethyl, ω-butoxybutyl, etc., a carboxyalkyl group, e.g., β-carboxyethyl, ω-carboxybutyl, etc., a sulfoalkyl group, e.g., β-sulfoethyl, ω-sulfobutyl, etc., a sulfatoalkyl group, e.g., β-sulfatoethyl, ω-sulfatobutyl, etc., an acyloxyalkyl group, e.g., β-acetoxyethyl, γ-acetoxypropyl, ω-butyryloxybutyl, etc., an alkoxycarbonylalkyl group, e.g., β-methoxycarbonylethyl, ω-ethoxycarbonylbutyl, etc., an aralkyl group, e.g., benzyl, phenethyl, etc., an alkenyl group, e.g., allyl, 1-propenyl, 2-butenyl, etc., or any aryl group of 6 to 20 carbon atoms, wherein "aryl" includes substituted aryl, e.g., phenyl, tolyl, naphthyl, methoxyphenyl, chlorophenyl, etc.; and $Z^1$ and $Z^2$ are the same or different and each represents the nonmetallic atoms necessary to complete a heterocyclic nucleus of the type used in cyanine dyes containing from 5 to 6 atoms in the heterocyclic ring, and which is of the type capable of being protonated at a pH of from about 6 to about 9. Particularly useful examples of $Z^1$ and $Z^2$ include benzimidazoles, such as 5-chloro-1,3-dialkyl benzimidazoles, 5-chloro-1,3-diaryl benzimidazoles, 5,6-dichloro-1,3-dialkyl benzimidazoles, 5,6-dichloro-1,3-diaryl benzimidazoles, 5-methoxy-1,3-dialkyl benzimidazoles, 5-methoxy-1,3-diaryl benzimidazoles, 5-cyano-1,3-dialkyl benzimidazoles, 5-cyano-1,3-diaryl benzimidazoles, and a 3,3-dialkyl-3H-indole nucleus, e.g., 3,3-dimethyl-3H-indole, 3,3-dimethyl-5- or 6-methoxy-3H-indole, etc. Any of the aforementioned cyanine dyes is a suitable chromogen.

The above-described cyanine dyes are conventional and their synthesis proceeds along well known lines, such as those described in Mees-James, Theory of the Photographic Process, 3rd Edition, pages 206–207.

Other dyes useful in this invention are protonated, nitrosubstituted dyes which deprotonate from the following formula, in a basic environment:

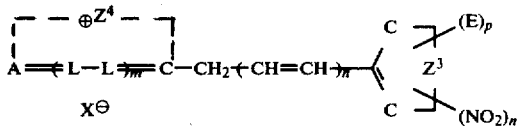

wherein:

a. k represents 0 or 1;

b. m represents 0 or 1;

c. n represents 1 or 2;

d. each L represents a methine group, including substituted methine groups, (e.g., —C═, —C(CH₃)═, etc.);

e. A represents an electron donating moiety, such as oxygen (—O—), sulfur (—S—), or $$-\underset{\underset{R^3}{|}}{N}-;$$

f. E is an electron-withdrawing group selected from the class consisting of nitro, cyano, ethoxycarbonyl, and halogenated methyl, g. p represents 0 or 1;

h. $R^3$ represents (1) an alkyl group having from 1 to 18 carbon atoms and preferably a lower alkyl group having from 1 to 4 carbon atoms (e.g., methyl, ethyl, propyl, isopropyl, butyl, secondary-butyl, isobutyl, tert-butyl, pentyl, hexyl, octyl, decyl, dodecyl, octadecyl); a sulfoalkyl group, preferably sulfo lower alkyl containing from 1 to 4 carbon atoms in the alkyl moiety (e.g., β-sulfoethyl, γ-sulfopropyl, γ-sulfobutyl, δ-sulfobutyl, etc.); a carboxyalkyl group, preferably a carboxy lower alkyl containing from 1 to 4 carbon atoms in the alkyl moiety (e.g., β-carboxyethyl, γ-carboxypropyl, δ-carboxybutyl, etc.); a sulfatoalkyl group, preferably a sulfato lower alkyl containing from 1 to 4 carbon atoms in the alkyl moiety (e.g., β-sulfatoethyl, γ-sulfatopropyl, δ-sulfatobutyl, etc.); an alkoxyalkyl group, preferably a lower alkoxy lower alkyl containing from 1 to 4 carbon atoms in both the alkoxy and alkyl moieties (e.g., β-methoxyethyl, γ-methoxypropyl, δ-propoxybutyl, etc.); an acyloxyalkyl group, preferably an acyloxy lower alkyl containing from 1 to 4 carbon atoms in the alkyl moiety (e.g., acetyloxyethyl, propanoyloxyethyl, butanoyloxybutyl, benzoyloxyethyl, toloyloxypropyl, etc.); an alkoxycarbonylalkyl group, preferably a lower alkoxy carbonyl lower alkyl containing 1 to 4 carbon atoms in both the alkoxy and alkyl moieties (e.g., β-methoxycarbonylethyl, δ-ethoxycarbonylbutyl, β-butoxycarbonylethyl, etc.); a dialkylaminoalkylene group, preferably a di-lower alkylamino lower alkylene containing 1 to 4 carbon atoms in the alkylene and alkyl moieties (e.g., dimethylaminoethylene, diethylaminopropylene, diethylaminobutylene, etc); a cycloaminoalkylene group, preferably cycloamino lower alkyl containing 4 to 6 atoms in the cycloamino moiety and 1 to 4 atoms in the alkyl moiety (e.g., pyrrolidinylethylene, morpholinopropylene, piperidinobutylene, pyrrolinylmethylene, etc); (2) an alkenyl group (including a substituted alkenyl group), preferably a lower alkenyl containing 2 to 4 carbon atoms (e.g., ethyl, allyl, 1-propenyl, 1-butenyl, 2-butenyl, etc.), or (3) an aryl group (including a substituted aryl)—e.g., phenyl, naphthyl, tolyl, xylyl, halophenyl, such as p-chlorophenyl, p-bromophenyl, etc., alkoxyphenyl such as methoxyphenyl, 2,4-dichlorophenyl, etc. and an aralkyl group, preferably an aryl lower alkyl containing from 1 to 4 carbon atoms in the alkyl moiety (e.g., benzyl, β-phenethyl, ω-phenylbutyl, etc.);

i. $X^{\Theta}$ represents an acid anion, such as chloride, bromide, p-toluenesulfonate, methanesulfonate, ethanesulfonate, methyl sulfate, ethyl sulfate, perchlorate, etc.;

j. $Z^3$ represents the atoms necessary to complete an aryl (preferably phenyl or naphthyl) ring which, by the presence of the nitro-substituent(s) and the "E" substituent is ortho- and/or para-nitro-substituted and may also be ortho- or para-substituted with another electron withdrawing group and which can have other substituents attached to it and other carbocyclic rings fused to it (e.g., 2-nitrophenyl, 2,4-dinitrophenyl, 4-nitrophenyl, 2,6-dinitrophenyl, 2,4,6-trinitrophenyl, 2-nitronaphthyl, 2,4-dinitronaphthyl, 2-nitro-4-cyanophenyl, 2-nitro-4-ethoxycarbonylphenyl, 4-nitro-2-trifluoromethylphenyl, and the like; and k. $Z^4$ represents the nonmetallic atoms necessary to complete a heterocyclic nucleus of the type used in cyanine dyes containing 5 or 6 atoms in the heterocyclic ring containing the electron-donating atom of the formula, which ring can contain a second hetero atom such as oxygen, nitrogen, selenium or sulfur. The heterocyclic nucleus preferably is selected from the group consisting of a thiazole nucleus including substituted and unsubstituted benzothiazole and naphthothiazole nuclei and the like, (e.g., thiazole, 4-methylthiazole, 4-phenylthiazole, 4,5-diphenylthiazole, 4-(2-thienyl)thiazole, benzothiazole, 4-chlorobenzothiazole, 4-methylbenzothiazole, 4-methoxybenzothiazole, 4-ethoxybenzothiazole, 4-phenylbenzothiazole, 5-chlorobenzothiazole, 5-bromobenzothiazole, 5-methylbenzothiazole, 5,5-methoxybenzothiazole, 5-ethoxybenzothiazole, 5-phenylbenzothiazole, 6-chlorobenzothiazole, 6-bromobenzothiazole, 6-methylbenzothiazole, 6-methoxybenzothiazole, 6-ethoxybenzothiazole, 5-methoxynaphtha[2,3-d]thiazole, β-naphthothiazole, α-naphthothiazole, 5-nitrobenzothiazole, 6-nitrobenzothiazole, 5-chloro-6-nitrobenzothiazole, etc.); an oxazole nucleus including substituted and unsubstituted benzoxazole and naphthoxazole nuclei and the like, (e.g., oxazole, 4-phenyl-oxazole, benzoxazole, 5-chlorobenzoxazole, 5-methylbenzoxazole, 5-bromobenzoxazole, 5-methoxybenzoxazole, 5-ethoxybenzoxazole, 5-phenylbenzoxazole, 5-methoxynaphthoxazole, 5-nitrobenzoxazole, 6-nitrobenzoxazole, 5-chloro-6-nitrobenaoxazole, etc.); a selenazole nucleus including substituted and unsubstituted benzoselenazole and naphthoselenazole nuclei and the like, (e.g., selenazole, 4-methylselenazole, 4-nitroselenazole, 4-phenylselenazole, benzoselenazole, 5-chlorobenzoselenazole, 6-chlorobenzoselenazole, naphtho[2,1-d]selenazole, 5-nitrobenzoselenazole, 6-nitrobenzoselenazole, 5-chloro-6-nitrobenzoselenazole, nitro group-substituted naphthoselenazoles, etc.); a thiazoline nucleus, (e.g, thiazoline, 4-methylthiazoline, 4-nitrothiazoline, etc.); a 2-pyridine nucleus (e.g., 2-pyridine, 5-methyl-2-pyridine, etc.); a 4-pyridine nucleus, (e.g., 4-pyridine, 3-methyl-4-pyridine, nitro group-substituted pyridines, etc.); a 3,3-dialkylindolenine nucleus (e.g., 3,3-dimethylindolenine, 3,3-diethyl-5 or 6-cyanoindolenine, 3,3-diethyl-5 or 6-nitroindolenine, 3,3-dimethyl-5 or 6-nitroindolenine, etc.); an imidazole nucleus, (e.g., imidazole, 1-alkylimidazole, benzimidazole, 1,3-dialkyl, 1,3-diaryl or 1-alkyl-3-arylimidazoles and benzimidazoles, such as 5-chloro-1,3-dialkylbenzimidazoles, 5-chloro-1,3-diarylbenzimidazoles, 5,6-dichloro-1,3-diarylbenzimidazoles, 5-methoxy-1,3-dialkylbenzimidazoles, 5-methoxy-1,3-diarylbenzimidazoles, 5-cyano-1,3-dialkylbenzimidazoles, 5-cyano-1,3-diarylbenzimidazoles, 1,3-dialkylnaphth[1,2-d]imidazole, 1,3-diarylnaphth[2,1-d]imidazole, etc.); a quinoline nucleus, (e.g., quinoline, 6-methylquinoline, 6-methoxyquinoline, 6-ethoxyquinoline, 6-chloroquinoline, 4-methoxyquinoline, 4-methylquinoline, 8-methoxyquinoline, β-methylquinoline, 4-chloroquinoline, 6-nitroquinoline, etc.); an imidazo[4,5-b]quinoxaline nucleus (as described in Brooker and VanLare U.S. Pat. No. 3,431,111), (e.g., imidazo[4,5-b]quinoxaline, 1,3-dialkylimidazo[4,5-b]quinoxaline such as 1,3-diethylimidazo[4,5-b]quinoxaline, 6-chloro-1,3-diethylimidazo[4,5-b]quinoxaline, etc., 1,3-dialkenylimidazo[4,5-b]quinoxaline such as 1,3-dialkylimidazo[4,5-b]quinoxaline, 6-chloro-1,3-dialkylimidazo[4,5-b]quinoxaline, etc., 1,3-diarylimidazo[4,5-b]quinoxaline such as 1,3-diphenylimidazo[4,5-b]quinoxaline, 6-chloro-1,3-diphenylimidazo[4,5-b]quinoxaline, etc.); a 3H-pyrolo[2,3-b]pyridine nucleus, e.g., 3,3-dialkyl-3H-pyrrolo[2,3-b]pyridine, 3,3-diethyl-3H-pyrrolo[2,3-b]pyridine, 1,3,3-trialkyl-3H-pyrrolo[2,3-b]pyridine such as 1,3,3-triethyl-3H-pyrrolo[2,3-b]pyridine, etc.); and a thiazolo[4,5-b]quinoline nucleus, a pyrylium (including benzopyrylium, thiapyrylium and benzothiapyrylium) nucleus; and a dithiolinium nucleus.

Although some of these dyes are not light stable, this is not a serious defect in this instance, as the readout can be essentially instantaneous, leaving little opportunity for interfering dye-bleaching due to ambient light.

As with the cyanine dyes, the nitro-substituted dyes can be manufactured by conventional, well-known processes.

Still other useful indicators are phthalein dyes having either the formula

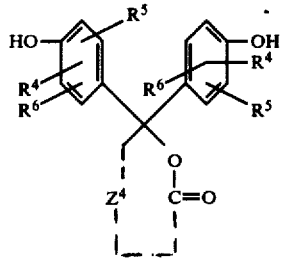

wherein $R^4$, $R^5$ and $R^6$ are the same or different, and are selected from the group consisting of halogen, hydrogen, alkyl and alkoxy having from 1 to 5 atoms, and $Z^4$ represents the atoms necessary to complete a ring-closing moiety selected from a naphthalide and phthalide; or the formula;

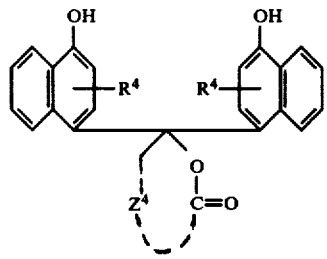

wherein $Z^4$ and $R^4$ are as above. Particularly useful indicator dyes include phenolsulfonephthalein, m-nitrophenol, 4-(4'-hydroxy-3-methoxybenzylidene)-phenethyl-2,3-dioxopyrrolidine, 4-(4-hydroxy-3-methoxybenzylidene)-1-methyl-2,3-dioxopyrrolidine, o-cresolsulfonephthalein, curcumin, m-cresolsulfonephthalein, 2,6-divanillylidenecyclohexanone, 4,4'-bis(4-amino-1-naphthylazo)-2,2'-stilbenedisulfonic acid, thymolsulfonephthalein, o-cresolphthalein, p-naphtholbenzein, phenolphthalein, ethyl, bis(2,4-dinitrophenol)acetate, and thymolphthalein.

Base bleachable dyes useful in this invention include styryl type dyes and pH sensitive pyrylium dyes. Such styryl type dyes are converted to colorless species by breaking the conjugated chain in an alkaline medium as in the following example;

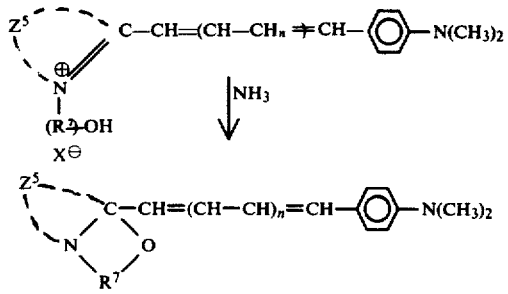

(3)

wherein $Z^5$ represents the non-metallic atoms necessary to complete a 3,3-disubstituted 3H-indole nucleus or fused analogs thereof, the 3,3 substituents of the nucleus taken separately each being a lower alkyl group containing from 1 to 5 carbon atoms or an aryl group containing from 6 to 12 carbon atoms, and when taken together these substituents being the atoms necessary to form an alicyclic ring; n is 0, 1 or 2; and $R^7$ is an alkylene group containing from 2 to 3 carbon atoms, such that $R^7$-OH is a hydroxyethyl or hydroxypropyl group, e.g., β-hydroxyethyl, δ-hydroxypropyl, and the like.

The formation of an indicator by the base-bleaching of a pyrylium dye proceeds by the elimination of the charged oxygen atom in the dye to form either a spiropyran or a pyridine. In the case of the spiropyran, the reaction can be written as

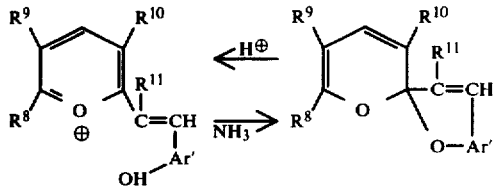

(4)

where $R^8$ and $R^9$ are alkyl groups containing from 1 to 10 carbon atoms or are the atoms required to complete an aromatic nucleus, $R^{10}$ and $R^{11}$ are the atoms required to form an alicyclic ring or are hydrogen or alkyl groups containing from 1 to 5 carbon atoms; and Ar' is an aryl group containing from 6 to 10 carbon atoms to which the hydroxyl group is attached in the ortho position. In the case of pyridine formation, the reaction can be written generally as

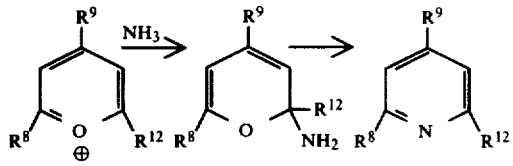

(5)

where $R^8$, $R^9$ and $R^{12}$ are each an alkyl group or aryl group containing from 1 to 10 carbon atoms.

Diazonium salts require the presence of a color coupler to form a dye in a basic environment such as is provided by $NH_3$. Many diazonium salts are known to the art to be useful dye formers. Typical of these salts are the benzene diazonium salts having the formula:

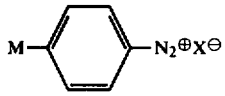

wherein M is either 1. a hydrogen atom,
2. a halogen atom,
3. an aryl radical
4. an amino radical including substituted amino radicals which can be cyclic radicals including the amino nitrogen atom and other hetero atoms such as oxygen, sulfur, nitrogen, etc.,
5. a mercapto radical, or
6. an alkyl or aryl thioether radical, and $X^{\ominus}$ is an acid anion. These compounds can also be substituted on one or more of the nuclear benzene carbons with, for example, at least one of a halogen atom, an aliphatic alkyl radical, an alkoxy radical, an acyl radical, a carbamyl radical, a carboxyl radical or a nitro radical. Aliphatic alkyl radicals are defined herein to include straight and branched chain alkyl radicals having from 1 to 8 carbon atoms such as methyl, ethyl, isopropyl, tert-butyl, n-pentyl, octyl and the like.

Particularly useful diazonium salts include p-aminobenzenediazonium salts having the formula as described above wherein M is either an amino radical including substituted amino radicals or a thioether radical such as described above, wherein the benzene nucleus is substituted or substituted in at least one of the 2-position and the 5-position with either an aliphatic alkyl radical or an alkoxy radical. This class of useful diazonium salts can be represented by the formula;

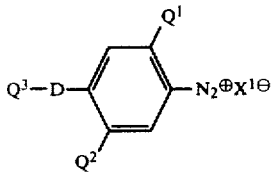

wherein

1. D is either a sulfur atom or a radical having the formula $NQ^4$,
2. $Q^3$, when taken alone, is either a hydrogen atom when D is $NQ^4$, or a lower aliphatic alkyl radical, a lower alkoxy radical, an acyl radical having the formula

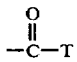

wherein T is either an aryl radical or an alkyl radical as described elsewhere herein, or a phenyl radical when D is either a sulfur atom or $NQ^4$, 3. $Q^4$, when taken alone, is either a hydrogen atom, a lower alkyl radical or a lower alkoxy radical,
4. $Q^3$ and $Q^4$, when taken together, complete a divalent radical having the formula;

$$-(CH_2)_a-O_b-(CH_2)_c-$$

wherein b is an integer having a value of 0 or 1, each of a and c is a positive integer, and the sum of a, b and c has 5. $Q^1$ and $Q^2$ are each either a hydrogen atom, a lower aliphatic alkyl radical (preferably methyl or ethyl) or a lower alkoxy radical (preferably methoxy or ethoxy), and $X^{1\ominus}$ is an acid anion.

Particularly useful p-aminobenzene diazonium salts include substituted aminobenzenediazonium salts having the formula;

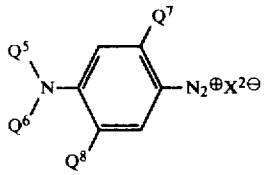

wherein 1. each of $Q^5$ and $Q^6$, when taken alone, is a lower alkyl radical,
2. $Q^5$ and $Q^6$, when taken together, are the number of carbon and hetero oxygen atoms necessary to complete a morpholino radical,
3. each of $Q^7$ and $Q^8$ is a hydrogen atom, a lower alkyl radical or a lower alkoxy radical, and
4. $X^{2\ominus}$ is either a chlorozincate anion, a fluoroborate anion, a sulfate anion, a phosphate anion, or a chlorostannate anion.

The most desirable benzenediazonium salts are the fluoroborate salts wherein:

1. $Q^7$ and $Q^8$ are alkoxy radicals when $Q^5$ and $Q^6$ complete a morpholino radical, and
2. $Q^7$ and $Q^8$ are each a hydrogen atom when $Q^5$ and $Q^6$ are each a lower alkyl radical.

Illustrative of the subject diazonium salts are such compounds as the salts of 1-diazo-2,5-dimethoxybenzene; 1-diazo-2,5-diethoxybenzene; 1-diazo-4-chloro-2,5-diethoxybenzene; 4-diazo-2,5-dimethoxybiphenyl; 4-diazo-2,5,4'-triethoxybiphenyl; 1-diazo-4-dimethylaminobenzene; 1-diazo-4-(diethoxyamino)benzene; 1-diazo-4-[bis(hydroxypropyl)amino]benzene; 1-diazo-4-(N-methyl-N-allylamino)benzene; 1-diazo-4-(diamylamino)benzene; 1-diazo-4-(oxazolidino)benzene; 1-diazo-4-(cyclohexylamino)benzene; 1-diazo-4-(9-carbazolyl)benzene; 1-diazo-4-(dihydroxyethylamino)-3-methylbenzene; 1-diazo-4-dimethylamino-3-methylbenzene; 1-diazo-2-methyl-4-(N-methyl-N-hydroxypropylamino)benzene; 1-diazo-4-dimethylamino-3-ethoxybenzene; 1-diazo-4-diethylamino-3-chlorobenzene; 1-diazo-2-carboxy-4-dimethylaminobenzene; 1-diazo-3-(2-hydroxyethoxy)-4-pyrrolidinobenzene; 1-diazo-2,5-diethoxy-4-acetoxyaminobenzene; 1-diazo-4-methylamino-3-ethoxy-6-chlorobenzene; 1-diazo-2,5-dichloro-4-benzylaminobenzene; 1-diazo-4-phenylaminobenzene; 1-diazo-4-morpholinobenzene; 1-diazo-4-morpholino-3-methoxybenzene; 1-diazo-4-morpholino-2,5-dimethoxybenzene; 1-diazo-4-morpholino-2-ethoxy-5-methoxybenzene; 1-diazo-4-morpholino-2,5-dibutoxybenzene; 1-diazo-2,5-diethoxy-4-benzoylaminobenzene; 1-diazo-2,5-dibutoxy-4-benzoylaminobenzene; 1-diazo-4-ethylmercapto-2,5-diethoxybenzene; 1-diazo-4-tolylmercapto-2,5-diethoxybenzene; 2-nitro-4-piperidinobenzene diazonium hexafluorophosphate and the like as well as mixtures thereof.

Azo dye couplers which can be reacted with the diazonium salt to form an azo dye include a wide variety of chemical species such as those disclosed by Kosar, "Light-Sensitive Systems," John Wiley & Sons, Inc., New York (1965), pp. 220–240. Phenolic couplers are particularly useful, the more common classes including:

1. as blue couplers, 2-hydroxy-3-naphthanilides having the formula:

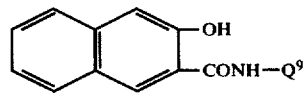

wherein $Q^9$ is a phenyl radical, and preferably a phenyl radical substituted with at least one of either a lower alkyl radical or a lower alkoxy radical or a halogen atom;

2. as blue couplers, ortho naphthalenediols, 3. as yellow couplers, 1-hydroxy-2-naphthamides having the formula:

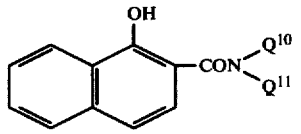

wherein a. each of $Q^{10}$ and $Q^{11}$, when taken alone, is a hydrogen atom or an aliphatic alkyl radical including substituted aliphatic alkyl radicals such as those described herein, a cycloalkyl radical, an aryl radical and like hydrocarbon or substituted hydrocarbon radicals, b. $Q^{10}$ and $Q^{11}$, when taken together, represent the carbon and oxygen atoms necessary to complete a six-membered hetero piperidino or morpholino radical, and 4. as yellow couplers, 2-acylamido-5-substituted phenols having the formula:

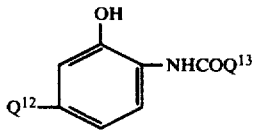

wherein $Q^{12}$ is either an alkyl radical or an alkoxy radical and $Q^{13}$ is an aliphatic alkyl radical, an aryl radical, an aralkyl radical or an aralkoxy radical.

Illustrative of the subject couplers are such compounds as for example, 2-hydroxy-3-naphthanilide; 2-hydroxy-2'-methyl-3-naphthanilide; 2-hydroxy-2',4'-dimethoxy-5'-chloro-3-naphthanilide; 2-hydroxy-2',4'-dimethoxy-3-naphthanilide; 2-hydroxy-2',5'-dimethoxy-4'-chloro-3-naphthanilide; 2-hydroxy-1'-naphthyl-3-naphthanilide; 2-hydroxy-2'-naphthyl-3-naphthanilide; 2-hydroxy-4'-chloro-3-naphthanilide; 2-hydroxy-2',5'-dimethoxy-3-naphthanilide; 2-hydroxy-2',4'-dimethyl-3-naphthanilide; 2,3-naphthalenediol; 1-hydroxy-2-naphthamide; N-methyl-1-hydroxy-2-naphthamide; N-butyl-1-hydroxy-2-naphthamide; N-octadecyl-1-hydroxy-2-naphthamide; N-phenyl-1-hydroxy-2-naphthamide; N-methyl-N-phenyl-1-hydroxy-2-naphthamide; N-(2-tetradecyloxyphenyl)-1-hydroxy-2-naphthamide; N-[4-(2,4-di-tert-pentylphenoxy)butyl]-1-hydroxy-2-naphthamide; 1-(1hydroxy-2-naphthoyl)-piperidine N-(3,5-dicarboxyphenyl)-N-ethyl-1-hydroxy-2-naphthamide; N,N-dibenzyl-1-hydroxy-2-naphthamide; N-(2-chlorophenyl)-1-hydroxy-2-naphthamide; N-(4-methoxyphenyl)-1-hydroxy-2-naphthamide; 1,3-bis(1-hydroxy-2-naphthamido)benzene; 2-acetamido-5-methylphenol; 2-acetamido-5-pentadecylphenyl; 2-butyramido-5-methylphenol; 2-(2,4-di-tert-pentylphenoxyacetamido)-5-methylphenol; 2-benzamido-5-methylphenyl; 3-(2-methoxyphenylcarbamoyl)-2-naphthol and the like, as well as mixtures thereof.

The indicator layer is thus comprised of the binder and any desired indicators, the binder being present in an amount from about 1.0 g/m$^2$ to about 20.0 g/m$^2$, and preferably 5.0 g/m$^2$ to about 15.0 g/m$^2$. The actual amount will of course depend upon the desired thickness of the test element. The concentration of indicator must be adequate to indicate the concentrations of the component being tested over the anticipated range and time of test. In the case of BUN analysis, the BUN range anticipated for various patients is from 0 to about 120 mg per deciliter of sample. The indicator must respond to this range, requiring an amount which ranges from about $3.0\times10^{-4}$ moles/m$^2$ to about $1\times10^{-2}$ moles/m$^2$, with the preferred amount being between $5\times10^{-4}$ and about $9.0\times10^{-4}$ moles/m$^2$.

Support

A support for all the preceding materials can be optionally provided, if the layers performing the other functions are not self-supporting.

The support, if used, can be comprised of a radiation (preferably light) transmitting, liquid-impermeable material. A variety of polymeric materials are well suited for this purpose, such as, for example, cellulose acetate, poly(ethylene terephthalate), polycarbonates, or polystyrene. The support may be of any suitable thickness typically from about 2 to about 10 mils. As will be described more fully below, it is desirable that the support be capable of transmitting at least certain wavelength bands of electromagnetic radiation in the range of between 200 and 900 nm. According to specifically preferred embodiments, it may be desirable to have the support selectively transmissive to specific relatively narrow wavelengths and opaque to all other wavelengths. In use the quantifiable product is fluorescent, the support should not fluoresce at an unacceptable level.

Layers discussed above can be coated directly on the support, or a subbing layer having energy transmission characteristics similar to those of the support may be used to aid in bonding the reagent layer to the support.

Alternatively, the support can be eliminated, particularly in those instances in which the binder of at least one of the other layers is self-supporting.

Cholesterol Analysis

Still another example of an element comprising two layers and a barrier composition separating the enzyme from the indicator is disclosed in commonly assigned U.S. Application Ser. No. 454,621, filed on Mar. 25, 1974 by Charles T. Goodhue et al, *now U.S. Pat. No. 3,983,005* entitled "Multilayer Analytical Elements [For Use in the Assay of Cholesterol]," refiled as a continuation-in-part application of Apr. 7, 1975, Ser. No. 565,897. In one embodiment of this application, the enzyme layer includes cholesterol oxidase, and a hydrolysis medium comprising a combination of protease and lipase which combination saponifies any cholesterol esters present in the sample to "free" cholesterol. Such a hydrolysis system is described in detail in commonly assigned U.S. Application Ser. No. 454,659, entitled "Method for the Enzymatic Hydolysis of Cholesterol," filed Mar. 25, 1974 in the names of Goodhue and Risley. According to this embodiment, the barrier composition is a hydrophilic polymeric material such as agarose; and the preferred indicator layer is a gelatin dispersion of peroxidase, an oxidizable alkyl amine and a naphthol capable of coupling with the oxidized amine. As one might expect the incorporation of a protease into a layer contiguous with an indicator layer whose matrix is composed primarily of gelatin poses certain stability problems since the protease attacks the proteinaceous gelatin as soon as wetting occurs. In this element the function of the barrier composition is to permit migration of a detectable product, namely hydrogen peroxide produced by the cholesterol oxidase-catalyzed reaction of cholesterol with oxygen, while prohibiting passage of the protease. It has been found that, in the embodiment shown in FIG. 5, only the cholesterol and not the esters are capable of penetrating the agarose to reach the enzymes in portion 18d. Accordingly, the uppermost indicator level should extend into the lowermost portion 54 of the spreading layer, at least to the extent that the protease and lipase enzymes are located there. The oxidase enzyme then is located in portion 18d.

The oxidation of the alkyl amine occurs as the result of free oxygen formed by the peroxidase induced decomposition of $H_2O_2$ which passes through the barrier layer from the enzyme layer. The reactions which occur in this assay are as follows:

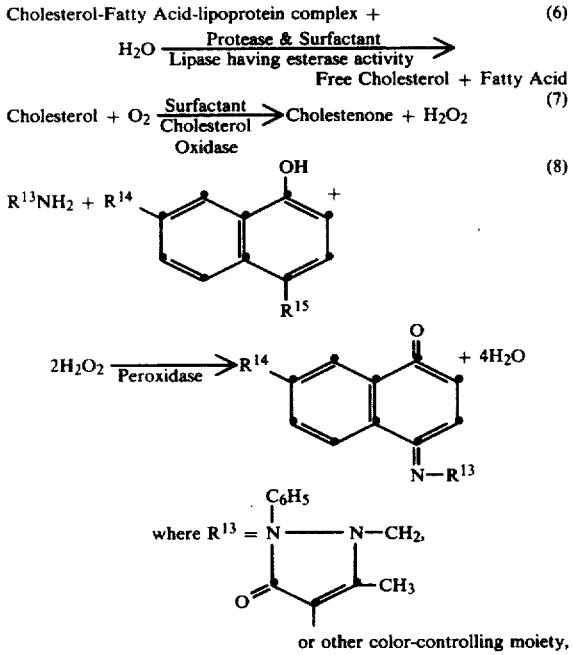

R 14 is hydrogen or hydroxy,
and $R^{15}$ is hydrogen or an alkoxy radical having from 1 to 2 carbon atoms.

Reaction (6) indicates the release of free cholesterol from cholesterol and cholesterol-esters complexed with serum lipo-proteins. Reaction (7) shows the cholesterol oxidase reaction. Reaction (8) demonstrates one of the many possible dye-peroxidase systems which may be used to detect $H_2O_2$ production. Here a system involving oxidation of 4-aminoantipyrine and subsequent coupling with the naphthol to form a compound with an absorption maximum at 490 nm is shown.

The barrier composition for this cholesterol assay element preferably is coated at a coverage ranging from about 0.1 to 1 g/m$^2$. A highly preferred embodiment of the present invention utilizes a layer of agarose at a coverage of from about 0.25 to about 0.70 g/m$^2$. Other examples of useful barrier compositions for a cholesterol detection element of this type include poly(acrylamide) resins such as poly(isopropylacrylamide).

Preparation

In preparing integral analytical elements of this invention heretofore described, the layers can be preformed separately and laminated to form the overall element. Layers prepared in such a manner are typically coated from solution or dispersion on a surface from which the dried layer can be physically stripped. However, a convenient method which can avoid the necessity for multiple stripping and lamination steps is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well known in the preparation of light-sensitive photographic films and papers. Interlayer adhesion problems can be overcome without harmful effect by means of surface treatments including extremely thin application(s) of subbing materials such as are used in photographic films.

If the layers described herein are formed by coating from solutions or dispersions as described in the aforementioned Pryzbylowicz et al application, it is often necessary to include coating aids which impart uniform coating properties to the various layers.

Whatever coating aids are used for this purpose, it is important that they do not inhibit the enzyme of the enzyme layer or any of the indicators present in the indicator layer. Particularly useful coating aids for this purpose include nonionic surfactants such as the octyl phenoxy polyethoxy ethanols commercially available from Rohm and Haas Co. under the Triton tradename (X-100, 102, 165, 305 and 405 being particularly useful), (p-nonylphenoxy) glycerol commercially available from Olin Mathieson Corp. under the tradename Surfactant 10G, and polyethylene glycols such as the Carbowax materials available from Union Carbide.

It may be appropriate to prepare an element, in accordance with the invention, having layers that are initially non-contiguous, and which further can be spaced apart, such as by the use of interleaves as described, for example, in U.S. Pat. No. 3,511,608 or by the use of a resilient absorbent material or deformable supports as described in U.S. Pat. No. 3,917,453 and U.S. Pat. No. 3,933,594. As will be appreciated, if the element has initially non-contiguous layers, it may be necessary to apply compressive force or otherwise provide means to bring layers of the element into fluid contact at the time of its use to provide an analytical result.

Use

In the use of the above analytical tape or element, the blood cells can first be separated from the serum, by such means as centrifuging, and the serum applied to the element. A particularly significant advantage of the analytical element described herein is its ability to be used to analyze either serum or whole blood. Of course, where energy transmission techniques are used, the spreading layer and any other layers must be uniformly permeable to the detecting radiation, and unless some mechanism is provided for removing the undesired residues of whole blood (e.g. wiping off or stripping off the spreading layer before measurement), it is preferable to use blood serum obtained in any fashion to make the analysis.

A typical automated analysis system utilizing the multilayer analytical element of this invention would provide means for disposing the element below a dispenser where a drop of the sample to be analyzed, such as whole blood or serum, would be applied to the surface of the element, then directing the element through one or more processing zones. The analytical measurement would typically be made by passing the element through a zone in which suitable apparatus for reflection, transmission or fluorescence spectrophotometry is provided.

Examples

By way of example only, the following are non-exhaustive specific illustrations of the above-described embodiments. Examples 1-6 are directed to elements for BUN analysis, while Example 7 concerns an element for cholesterol analysis as disclosed in the aforesaid continuation-in-part application of Ser. No. 454,621.

Examples 1-3

A series of 3 test elements for BUN having the format shown in FIG. 1, utilizing different chromogens in the indicator layer, was prepared in the following manner.

An ammonia-permeable, relatively water-impermeable indicator layer comprising the different chromogens numbered 1 through 3 below in Table 1, and cellulose acetate butyrate at 8.55 g/m$^2$ as coated on a poly(ethylene terephthalate) film support from a mixture of organic solvents consisting essentially of dichloroethane and acetone. Each of these coatings was overcoated with an ammonia-permeable, relatively water-impermeable layer of cellulose propionate valerate having 30% by weight valeryl content, at 0.84 g/m$^2$, coated from t-butyl alcohol. The elements were then overcoated with a buffered gelatin (pH 7.5) layer containing gelatin at 5.4 g/m$^2$, urease at 4300 U/m$^2$, dipotassium phosphate buffer at 0.05 g/m$^2$, bisvinylsulfonylmethyl ether as a hardener at 0.06 g/m$^2$, oleic ether of polyethylene glycol as a surfactant at 0.32 g/m$^2$, and ethylene diamine tetraacetic acid tetrasodium salt at 0.40 g/m$^2$.

To complete the element a reflecting-spreading layer comprising cellulose acetate at 6.6 g/m$^2$, titanium dioxide at 46.0 g/m$^2$, and Triton X-405 (an octyl phenoxy polyethoxy ethanol available from Rohm and Haas Co.) at 2.69 g/m$^2$ was applied from a mixture of acetone and dichloroethane (1:1) dual melted with xylene (6.4:1).

The completed analytical elements were tested in the following manner.

Aqueous solutions of reagent grade urea ($<10^{-5}$ M $NH_3$ contained in a 1 M solution) were prepared in the range 1 to 150 mg urea nitrogen/dl. The normal range in serum is 10 to 20 mg BUN/dl. These solutions were spotted on the test elements (10 μl spots). A spectrophotometer was used to measure the reflection densities generated at appropriate wavelengths. The measurements indicated in Table I were taken after 10 minutes incubation at 50° C.

TABLE I

| Ex. | Chromogen | Amt. of Chromogen | Wavelength of Measurement | Reflection Density urea concentration in mg/dl 5 mg/dl | 10 mg/dl | 20 mg/dl | 50 mg/dl | 100 mg/dl | 150 mg/dl |
|---|---|---|---|---|---|---|---|---|---|
| 1 | 1-methyl-2 (2,4-dinitrophenyl)methyl quinolinium perchlorate | 1.08 gm/m$^2$ | 585 nm | 0.62 | 1.06 | — | — | — | — |
| 2 | 6-(2,4-dinitrophenyl)-6H-pyrido[2,1-s]isoindolium perchlorate | 1.08 gm/m$^2$ | 610 nm | 0.45 | 0.81 | 1.22 | 2.06 | — | — |
| 3 | phenolsulfonephthalein sodium salt | 0.8 gm/m$^2$ | 565 nm | 0.13 | 0.20 | 0.44 | 0.71 | 0.90 | 0.96 |

Table I demonstrates the utility of analytical elements of the present invention. It is noted that, because of the high extinction coefficients (near $10^4$) of the chromogens of Examples 1 and 2, it is preferred that measurement be made using kinetic analysis, utilization of a shorter time of reaction, or reading the dye off-peak, for determination of concentrations of BUN in excess of 50 mg/dl.

EXAMPLE 4

An analytical element was prepared as follows: An indicator layer comprising the chromogen 1-ethyl-4(2,6-dinitrophenyl) methyl quinolinium ethyl sulfonate at 3.78 g/m$^2$ and cellulose acetate at 6.43 g/m$^2$ was coated on a polyethylene terephthalate film support from a mixture comprised of methanol and acetone (1:2). An ammonia permeable barrier layer of cellulose acetate butyrate having a 27% butyryl content and 21% acetyl content was coated over the indicator layer at 0.8 g/m$^2$ from dichloroethane. A subbing layer of copoly(-methylmethacrylate, methacryloyloxytrimethyl ammonium methyl sulfate; 2-hydroxypropyl acrylate; 2-acetoacetoxyethyl methacrylate) in the ratio of 40:20:20:20 at 0.14 g/m$^2$ was then applied from acetone.

The element was then overcoated with a gelatin layer buffered at a pH of 8.0 comprising deionized gelatin at 21.6 g/m$^2$, oleyl ether of polyethylene glycol at 0.65 g/m$^2$, ethylene diamine tetraacetic acid tetrasodium salt at 0.4 g/m$^2$, N,N-bis(2-hydroxyethyl)glycine at 5.4 g/m$^2$, disodium orthophosphate at 0.28 g/m$^2$, dithiothreitol at 0.9 mg/m$^2$, urease at 27,000 U/m$^2$, and bisvinylsulfonylmethyl ether at 0.13 g/m$^2$. A subbing layer of poly-(N-isopropylacrylamide) at 0.32 g/m$^2$ was applied from acetone. A spreading-reflecting layer was overcoated as described in Example 1.

The completed analytical element was evaluated in the following manner. Aqueous solutions containing 7 percent albumin and reagent grade urea in concentrations from 0 to 150 mg urea nitrogen/dl were prepared. These solutions were then applied to the test element in 10 μl aliquots. A spectrophotometer having an interference filter covering a band of 30 nm centered at 463 nm, a Wratten 2B filter and a 0.4 neutral density filter, with an incubation temperature of 40° C., was used to measure the reflection densities after 5 minutes. The following results were obtained.

| mg Urea Nitrogen/dl in 7% Albumin Solution | Reflection Density (5 minutes at 40° C.) |
|---|---|
| 0 | 0.04 |
| 10 | 0.26 |
| 25 | 0.57 |
| 50 | 0.97 |
| 100 | 1.69 |
| 150 | 2.33 |

EXAMPLE 5

An ammonia-permeable, relatively water-impermeable layer containing a diazo coupling system as the indicator was prepared in the following manner.

A sample of 7 mil poly(ethylene terephthalate) film support subbed with gelatin was coated with a layer comprising (1) cellulose acetate butyrate having a 27 weight percent butyryl content and 21% acetyl content at 3.19 g/m$^2$, (2) 2-nitro-4-piperidinobenzene diazonium hexafluorophosphate at 0.635 g/m$^2$, (3) 3-(2-methoxyphenylcarbamoyl)-2-naphthol at 0.84 g/m$^2$, and (4) the oleic ether of polyethylene glycol 1540 at 0.097 g/m$^2$.

The coated element, a light cream color, was then tested by spotting with ammonium hydroxide solutions of concentrations equivalent to 10 and 40 mg percent urea, resulting in the generation of a light green and a darker green color respectively, illustrating the suitability of the diazonium salts as the dye precursor.

EXAMPLE 6

An ammonia-permeable, relatively water-impermeable layer containing an ammonia bleachable dye as the indicator was prepared in the following manner.

A sample of 7 mil poly(ethylene terephthalate) subbed as in Example 4 was coated with a layer comprising (1) cellulose acetate butyrate having a 27 weight percent butyryl content and 21% acetyl content at 3.22 g/m$^2$, and (2) 2[$\beta$-(2-hydroxy-1-naphthyl)-$\alpha$-methylvinyl]-1-benzopyrylium perchlorate at 0.322 g/m$^2$.

The coated element, which was dark blue in color, was then tested by spotting with ammonium hydroxide solutions of concentrations equivalent to 10 and 20 mg percent urea. The dark blue color of the element was partially bleached in the area which was spotted with the low concentration of ammonium hydroxide and completely bleached in the area spotted with the higher concentration of ammonium hydroxide. Since the urea equivalency thus tested covers the range of normal BUN, Example 6 illustrates the adequacy of bleachable dyes as the indicator.

EXAMPLE 7

An analytical element containing all the necessary materials for the quantitative analysis of total cholesterol in blood serum was prepared in the following manner. A sample of gelatin subbed 7 mil poly(ethylene terephthalate) film support was coated with an indicator layer comprising gelatin (21.5 g/m$^2$), peroxidase (7,000 U/m$^2$), 4-methoxy-1-naphthol (750 mg/m$^2$), 4-aminoantipyrine hydrochloride (635 mg/m$^2$) and 4-amino-5,6-dihydroxy-2-methylpyrimidine (10.8 mg/m$^2$) at a pH of 7.0. A barrier layer comprising agarose (108 mg/m$^2$) was then applied followed by an interlayer comprising poly(n-isopropylacrylamide) (323 mg/m$^2$) and a spreading and enzyme layer comprising cellulose acetate (9.7 g/m$^2$), titanium dioxide (64.5 g/m$^2$), Lipase M (1.08 g/m$^2$), $\alpha$-chymotrypsin (2.15 g/m$^2$), Triton X-100, an octylphenoxy polyethoxy ethanol available from Rohm and Haas Co., (2.96 g/m$^2$), and cholesterol oxidase (450 U/m$^2$).

To evaluate the coated element a series of blood serum samples containing 122, 244 and 366 mg percent cholesterol were applied to the coated element (10 $\mu$l drops). After 12 minutes at 37° C. a spectrophotometer with a 660 nm interference filter was used to measure reflection density. A stepwise increase was detected for each increase in cholesterol, as follows:

| Test Serum (mg % Cholesterol) | $D_R$660 nm (12 min at 37° C.) |
|---|---|
| 122 | 0.12 |
| 244 | 0.21 |
| 366 | 0.31 |

EXAMPLES 8–17

In these examples, an element similar to the element of Example 1 was prepared, except that the indicator layer was prepared by coating 2.26 g/m$^2$ of 4(2,6-dinitro-4-chlorobenzyl)1-propyl quinolinium ethane sulfonate in cellulose acetate having 40% acetylation, so that the indicator layer itself incorporated a carrier composition, in addition to a separate barrier layer formed by cellulose acetate butyrate (27% butyryl content and 21% acetyl content) disposed between the indicator layer and the enzyme layer. The enzyme layer was buffered to a pH of about 8.0.

The analytical elements were evaluated in the following manner:

Aqueous solutions containing albumin and reagent grade urea in 4 concentrations ranging from about 15 to about 115 mg urea nitrogen/dl were prepared. These solutions were then applied to the test element in 10 $\mu$l aliquots. Reflection densities at 670 nm were measured after 5 minutes. Results are shown in Table II.

Table II

| | Amounts of BUN (mg/dl) | | | |
|---|---|---|---|---|
| Example | 15.2 | 30.0 | 74.3 | 114.5 |
| 8 | 0.4251 | 0.6567 | 1.3280 | — |
| 9 | 0.4156 | 0.6475 | 1.3433 | 1.8942 |
| 10 | 0.4117 | 0.6403 | 1.3090 | 1.8859 |
| 11 | 0.4151 | 0.6627 | 1.3152 | 1.9255 |
| 12 | 0.4234 | 0.6536 | 1.3566 | 1.9097 |
| 13 | 0.4113 | 0.6546 | 1.3171 | 1.8790 |
| 14 | 0.4099 | 0.6559 | 1.3106 | 1.8739 |
| 15 | 0.4121 | 0.6428 | 1.3230 | 1.9024 |
| 16 | 0.4157 | 0.6586 | — | 1.8650 |
| 17 | 0.4094 | 0.6549 | 1.3335 | 1.8800 |
| mean | 0.4149 | 0.6528 | 1.3268 | 1.8906 |
| SD | 0.0054 | 0.0071 | 0.0163 | 0.0192 |
| % COV | 1.30 | 1.08 | 1.23 | 1.01 |

While the invention has been described in detail with particular reference to preferred embodiments thereof, it will be understood that variations and modifications can be effected within the spirit and scope of the invention.

What is claimed is:

1. In an integral element useful in the analysis of a fluid sample for a predetermined analyte, the element including 1. a reagent capable of interacting in the presence of said analyte to produce a decomposition product; and 2. a reagent capable of interacting with said decomposition product or an intermediate to provide a detectable change;

the improvement comprising a barrier composition separating substantially all of [said] said reagent (1) from said reagent (2), said barrier composition being substantially uniformly permeable to said decomposition product and substantially impermeable to interferants.

2. An element as defined in claim 1, wherein said reagents are uniformly distributed in separate layers and said barrier composition is in a layer between said separate layers or in one of said separate layers.

3. An element as defined in claim 2 wherein said barrier composition is substantially impermeable to liquid water and wherein said decomposition product is a vapor.

4. An element as defined in claim 1 wherein said composition includes a member selected from the group consisting of cellulose propionate valerate, cellulose acetate butyrate, cellulose acetate, and poly(methyl methacrylate).

5. In an integral, multilayered element useful in the analysis of a fluid sample for a predetermined analyte, the element including, in superposed relationship:

1. a first layer which includes at least one reagent capable of interacting in the presence of the analyte to produce a decomposition product; and
2. a second layer which includes at least one reagent capable of interacting in the presence of said decomposition product or an intermediate to provide a detactable change;

the improvement comprising a barrier composition separating substantially all of said reagents in said first and second layers from one another, said composition being substantially uniformly permeable to said decomposition product and substantially impermeable to interferants;

one of said reagents being distributed within said barrier composition.

6. An element as defined in claim 5 wherein said first layer reagent includes at least one enzyme capable of complexing with analyte to produce a decomposition product capable of reacting with said distributed reagent to produce said detectable species; and further including a non-fibrous isotropically porous spreading layer.

7. An element as defined in claim 6 wherein said enzyme is confined to a discrete layer interposed between said spreading layer and said barrier composition.

8. An element as defined in claim 5 wherein said barrier composition is substantially impermeable to liquid water and wherein said decomposition product is a vapor.

9. An element as defined in claim 8 wherein said composition includes a member selected from the group consisting of cellulose propionate valerate, cellulose acetate butyrate, cellulose acetate, and poly(methyl methacrylate).

10. In an integral, multilayered element useful in the analysis of a fluid sample for a predetermined analyte, the element including, in superposed relationship:

1. a first layer which includes at least one reagent capable of interacting in the presence of the analyte to produce a decomposition product; and
2. a second layer which includes at least one reagent capable of interacting with said decomposition product or an intermediate to provide a detectable change;

the improvement comprising a barrier composition separating substantially all of said first and second layer reagents from one another, said barrier composition being substantially permeable to said decomposition product and substantially uniformly impermeable to interferants;

said barrier composition being contiguous with and between said two layers.

11. An element as defined in claim 10 wherein said first layer reagent includes at least one enzyme capable of complexing with a predetermined analyte to produce a decomposition product capable of reacting with said second layer reagent to produce said detectable change; and further including an isotropically porous spreading layer.

12. An element as defined in claim 11 wherein said enzyme is generally confined to a layer distinct from and between said spreading layer and said barrier composition.

13. An element as defined in claim 12 wherein said composition includes a member selected from the group consisting of cellulose propionate valerate, cellulose acetate butyrate, cellulose acetate, and poly(methyl methacrylate).

14. In an integral element useful in the analysis of a fluid sample for urea, the element including 1. urease; and
2. a reagent capable of interacting with ammonia to form a detectable product;

the improvement comprising a barrier composition separating substantially all of said urease from said reagent, said composition being substantially uniformly permeable to ammonia vapor and substantially impermeable to liquid bases.

15. An element as defined in claim 14 wherein said reagent includes a dye precursor which, in the presence of $NH_3$, produces a dye.

16. An element as defined in claim 15 wherein said dye precursor is a leuco compound which deprotonates in the presence of $NH_3$.

17. An element as defined in claim 16 wherein said leuco compound is a leuco dye selected from the group consisting of leuco cyanine dyes, nitro-substituted leuco dyes, and leuco phthalein dyes.

18. An element as defined in claim 17 and for the analysis of BUN, wherein said leuco dye is present in an amount sufficient to provide deprotonation in response to all the ammonia transmited to the leuco dye during the time of the analysis and corresponding to a range of from 0 to about 120 mg of BUN per deciliter of sample.

19. In an integral element useful in the analysis of a fluid sample for urea, the element including 1. urease; and
2. a reagent capable of interacting with ammonia to form a detectable product;

the improvement comprising a barrier composition separating said urease and said reagent, said composition being substantially uniformly permeable to ammonia vapor and substantially impermeable to liquid bases, said reagent including a 1,2-substituted quinolinium salt which deprotonates in the presence of $NH_3$ to produce a dye.

20. In an integral element useful in the analysis of a fluid sample for urea, the element including 1. urease; and
2. a reagent capable of interacting with ammonia to form a detectable product;

the improvement comprising a barrier composition separating said urease and said reagent, said composition being substantially uniformly permeable to ammonia vapor and substantially impermeable to liquid bases, said reagent including a 1,4-substituted quinolinium salt which deprotonates in the presence of $NH_3$ to produce a dye.

21. In an integral element useful in the analysis of a fluid sample for urea, the element including 1. urease; and
2. a reagent capable of interacting with ammonia to form a detectable product;

the improvement comprising a barrier composition separating said urease and said reagent, said composition being substantially uniformly permeable to ammonia vapor and substantially impermeable to liquid bases, said reagent including a leuco dye that deprotonates in the presence of $NH_3$ and has the formula

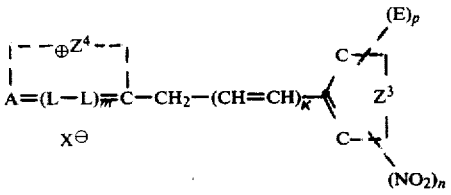

wherein:

a. k represents 0 or 1;
b. m represents 0 or 1;
c. n represents or 2;
d. each L represents a methine group;
e. A represents an electron donating moiety, selected from the group oxygen (—O—), sulfur (—S—), and

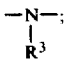

f. E is an electron-withdrawing group selected from the class consisting of nitro, cyano, ethoxycarbonyl, and halogenated methyl;
g. p represents 0 or 1;
h. $R^3$ represents either an alkyl group having from 1 to 18 carbon atoms and preferably a lower alkyl group having from 1 to 4 carbon atoms, a sulfoalkyl group, a carboxyalkyl group, a sulfatoalkyl group, an alkoxyalkyl group, an acyloxyalkyl group, an alkoxycarbonylalkyl group, a dialkylaminoalkylene group, a cycloaminoalkylene group, an alkenyl group, or an aryl group;
i. $X^{\ominus}$ is an acid anion;
j. $Z^3$ represents the atoms necessary to complete an aryl ring; and
k. $Z^4$ represents the nonmetallic atoms necessary to complete a heterocyclic nucleus.

22. An element as defined in claim 21 wherein said leuco dye is 1-ethyl-4(2,6-dinitrophenyl)methyl quinolinium ethyl sulfonate.

23. An element as defined in claim 21 wherein said leuco dye is 1-methyl-2(2,4-dinitrophenyl)methyl quinolinium perchlorate.

24. An element as defined in claim 21 wherein said leuco dye is 1-ethyl-4(2,4-dinitro-1-naphthyl)methyl quinolinium chloride.

25. An element as defined in claim 21 wherein said leuco dye is 1-propyl-4(2,6-dinitro-4-chlorophenyl)-methyl quinolinium ethane sulfonate.

26. In an integral element useful in the analysis of a fluid sample for urea, the element including 1. urease; and
2. a reagent capable of interacting with ammonia to form a detectable product;

the improvement comprising a barrier composition separating said urease and said reagent, said composition being substantially uniformly permeable to ammonia vapor and substantially impermeable to liquid bases, said reagent including a dye precursor that deprotonates in the presence of $NH_3$ and has the formula

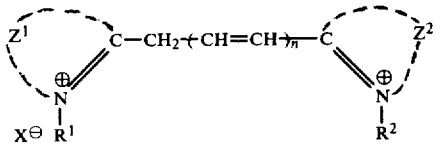

(I)

wherein:

n represents a positive integer of 1 to 10;
$X^{\ominus}$ represents an acid anion;
$R^1$ and $R^2$ are the same or different and each represents either hydrogen, a substituted or unsubstituted alkyl group, an alkoxyalkyl group, a carboxyalkyl group, a sulfoalkyl group, a sulfato alkyl group, an acyloxyalkyl group, an alkoxycarbonylalkyl group, an aralkyl group, an alkenyl group, or a substituted or unsubstituted aryl group; and
$Z^1$ and $Z^2$ are the same or different and each represents the nonmetallic atoms necessary to complete a heterocyclic nucleus.

27. In an integral element useful in the analysis of a fluid sample for urea, the element including 1. urease; and
2. a reagent capable of interacting with ammonia to form a detectable product;

the improvement comprising a barrier composition separating said urease and said reagent, said composition being substantially uniformly permeable to ammonia vapor and substantially impermeable to liquid bases, said reagent including an ammonia-bleachable dye.

28. An element as defined in claim 27 wherein said dye is a pyrylium dye or styryl dye.

29. An integral multilayered element useful in the analysis of a fluid sample for a predetermined analyte, the element comprising, in superposed relationship, 1. a first layer which includes an enzyme capable of complexing with analyte to produce a decomposition product;
2. a second layer which includes a reagent capable of interacting with said decomposition product or an intermediate to form a detectable change;

3. a barrier composition separating substantially all of said enzyme from said reagent, said composition being substantially uniformly permeable to said decomposition product and substantially impermeable to interferants; and 4. a non-fibrous isotropically porous spreading layer.

30. An element as defined in claim 29 wherein said spreading layer includes means for reflecting light.

31. An element as defined in claim 30 wherein said means includes titanium dioxide.

32. An integral element useful in the analysis of a fluid sample for a predetermined analyte, the element comprising 1. an enzyme capable of complexing with said analyte to produce a decomposition product;

2. a dye precursor capable of forming a detectable change and having the formula

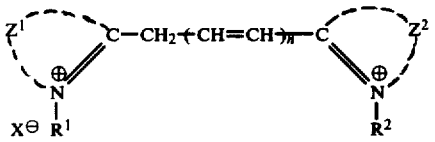

(1)

wherein:

n represents a positive integer of 1 to 10;

$X^{\ominus}$ represents an acid anion;

$R^1$ and $R^2$ are the same or different and each represents either hydrogen, a substituted or unsubstituted alkyl group, an alkoxyalkyl group, a carboxyalkyl group, a sulfoalkyl group, a sulfato alkyl group, an acyloxyalkyl group, an alkoxycarbonylalkyl group, an aralkyl group, an alkenyl group, or a substituted or unsubstituted aryl group; and $Z^1$ and $Z_2$ are the same or different and each represents the nonmetallic atoms necessary to complete a heterocyclic nucleus; and 3. a barrier composition separating said enzyme and said dye, said composition being substantially uniformly permeable to said decomposition product and substantially impermeable to interferants.

33. A process of analyzing a liquid for the presence of a predetermined analyte, comprising the steps of a. depositing a sample of the liquid on an element comprising a first reagent capable of producing a radiant energy detectable species and having in association with it a binder, a second reagent capable of producing from the analyte a decomposition product which is interactive with said first reagent; and a barrier composition separating substantially all of said second reagent from said first reagent, said composition being substantially uniformly permeable to said decomposition product and substantially impermeable to interferants;

whereby the analyte and the second reagent react to produce a decomposition product that selectively permeates through the barrier composition where it reacts with the first reagent; and b. measuring said detectable change.

34. In an integral multilayered element useful in the analysis of a fluid sample for a predetermined analyte, the element including, in superposed relationship:

1. a first layer which includes a sample intercept area, and reagent in said area capable of interacting with the analyte to produce a decomposition product; and 2. a second layer which includes at least one reagent capable of interacting with said decomposition product or an intermediate to form a detectable change;

the improvement comprising a barrier composition separating substantially all of said first and second layer reagent from one another and having a sample intercept area that is at least coextensive with said sample intercept area of said first layer, said composition within its sample intercept area being uniformly permeable to said decomposition product and impermeable to interferants.

35. An element as defined in claim 34 wherein said barrier composition is substantially impermeable to liquid water and wherein said decomposition product is a vapor.

36. In an integral, multilayered element useful in the analysis of a fluid sample for a predetermined analyte, the element including, in superposed relationship:

1. a first layer which includes a sample intercept area and a reagent in said area capable of interacting with the analyte to produce a decomposition product; and 2. a second layer which includes a reagent capable of interacting with said decomposition product or an intermediate to form a detectable change;

the improvement comprising a barrier composition separating substantially all of said first and second layer reagents from one another and having a sample intercept area that is at least coextensive with said sample intercept area of said first layer, said barrier composition within said sample intercept area being uniformly impermeable to interferants;

said barrier composition incorporating one of said reagents within said coextensive sample intercept area.

37. An element as defined in claim 36 wherein said first layer reagent includes an enzyme capable of complexing with the analyte being tested to effect a decomposition product capable of reacting with said incorporated reagent to produce said detectable species, and further including a non-fibrous isotropically porous spreading layer.

38. An element as defined in claim 37 wherein said enzyme is confined to a layer separate and distinct from the spreading layer between said spreading layer and said barrier composition.

39. An element as defined in claim 36 wherein said barrier composition includes a member selected from the group consisting of cellulose propionate valerate, cellulose acetate butyrate, cellulose acetate, and poly(methyl methacrylate).

40. In an integral element useful in the analysis of a fluid sample for urea, the element including 1. a layer comprising urease in a sample intercept area; and 2. a reagent capable of interacting with ammonia to form a detectable change;

the improvement comprising a barrier composition separating substantially all of said urease from said reagent and having a sample intercept area that is at least coextensive with the sample intercept area of the layer comprising said urease, said barrier composition within its sample intercept area being uniformly permeable to ammonia vapor and impermeable to liquid base.

41. An element as defined in claim 40 wherein said barrier composition is substantially impermeable to liquid water.

42. An element as defined in claim 40 wherein said one reagent includes a leuco compound which deprotonates in the presence of $NH_3$.

43. An element as defined in claim 42 wherein said compound is selected from the group consisting of leuco cyanine dyes, nitro-substituted leuco dyes, and leuco phthalein dyes.

44. In an integral element useful in the analysis of a fluid sample for urea, the element including 1. a layer comprising urease in a sample intercept area; and
2. a reagent capable of interacting with ammonia to form a detectable change;

the improvement comprising a barrier composition separating said urease and said reagent and having a sample intercept area that is at least coextensive with the sample intercept area of the layer comprising said urease, said barrier composition within its sample intercept area being uniformly permeable to ammonia vapor and impermeable to liquid bases, said reagent including a 1,2-substituted quinolinium salt which deprotonates in the presence of $NH_3$.

45. In an integral element useful in the analysis of a fluid sample for urea, the element including 1. a layer comprising urease in a sample intercept area; and
2. a reagent capable of interacting with ammonia to form a detectable change;

the improvement comprising a barrier composition separating said urease and said reagent and having a sample intercept area that is at least coextensive with the sample intercept area of the layer comprising said urease, said barrier composition within its sample intercept area being uniformly permeable to ammonia vapor and impermeable to liquid bases, said reagent including a 1,4-substituted quinolinium salt which deprotonates in the presence of $NH_3$.

46. In an integral element useful in the analysis of a fluid sample for urea, the element including 1. a layer comprising urease in a sample intercept area; and
2. a reagent capable of interacting with ammonia to form a detectable change;

the improvement comprising a barrier composition separating said urease and said reagent and having a sample intercept area that is at least coextensive with the sample intercept area of the layer comprising said urease, said barrier composition within its sample intercept area being uniformly permeable to ammonia vapor and impermeable to liquid bases, said reagent including a leuco dye that deprotonates in the presence of $NH_3$ and has the formula

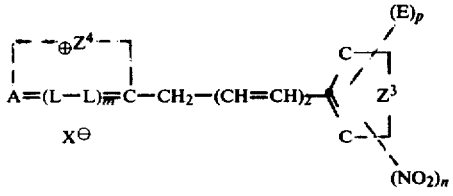

wherein:

a. k represents 0 or 1;
b. m represents 0 or 1;
c. n represents 1 or 2;
d. each L represents a methine group;
e. A represents an electron donating moiety, selected from the group oxygen (—O—), sulfur (—S—), and

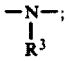

f. E is an electron-withdrawing group selected from the class consisting of nitro, cyano, ethoxycarbonyl, and halogenated methyl;
g. p represents 0 or 1;
h. $R^3$ represents either an alkyl group having from 1 to 18 carbon atoms and preferably a lower alkyl group having from 1 to 4 carbon atoms, a sulfoalkyl group, a carboxyalkyl group, a sulfatoalkyl group, an alkoxyalkyl group, an acyloxyalkyl group, an alkoxycarbonyl alkyl group, a dialkylaminoalkylene group, a cycloaminoalkylene group, an alkenyl group, or an aryl group;
i. $X^{\ominus}$ is an acid anion;
j. $Z^3$ represents the atoms necessary to complete an aryl ring; and
k. $Z^4$ represents the nonmetallic atoms necessary to complete a heterocyclic nucleus.

47. In an integral element useful in the analysis of a fluid sample for urea, the element including 1. a layer comprising urease in a sample intercept area; and
2. a reagent capable of interacting with ammonia to form a detectable change;

the improvement comprising a barrier composition separating said urease and said reagent and having a sample intercept area that is at least coextensive with the sample intercept area of the layer comprising said urease, said barrier composition within its sample intercept area being uniformly permeable to ammonia vapor and impermeable to liquid bases, said reagent including a chromogen that deprotonates in the presence of $NH_3$ and has the formula

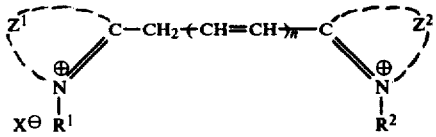

(1)

wherein:

n represents a positive integer of 1 to 10;
$X^{\ominus}$ represents an acid anion;
$R^1$ and $R^2$ are the same or different and each represents either hydrogen, an alkyl group, an alkoxyalkyl group, a carboxyalkyl group, a sulfoalkyl group, a sulfato alkyl group, an acyloxyalkyl group, an alkoxycarbonylalkyl group, an aralkyl group, an alkenyl group, or an aryl group; and
$Z^1$ and $Z^2$ are the same or different and each represents the nonmetallic atoms necessary to complete a heterocyclic nucleus.

48. In an integral element useful in the analysis of a fluid sample for urea, the element including 1. a layer comprising urease in a sample intercept area; and
2. a reagent capable of interacting with ammonia to form a detectable change;

the improvement comprising a barrier composition separating said urease and said reagent and having a sample intercept area that is at least coextensive with the sample intercept area of the layer comprising said urease, said barrier composition within its sample intercept area being uniformly permeable to ammonia vapor and impermeable to liquid bases, said reagent including an ammonia-bleachable dye.

49. An element as defined in claim 48 wherein said dye is a pyrylium dye or styryl dye.

50. An integral element useful in the analysis of a fluid sample for a predetermined analyte, the element comprising 1. a layer which includes an enzyme in a sample intercept area, capable of reacting with said analyte to produce a decomposition product;
2. a dye precursor having the formula

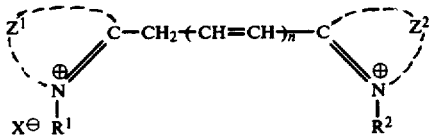

(1)

wherein:

n represents a positive integer of 1 to 10;

$X^{\ominus}$ represents an acid anion;

$R^1$ and $R^2$ are the same or different and each represents either hydrogen, an alkyl group, an alkoxyalkyl group, a carboxyalkyl group, a sulfoalkyl group, a sulfato alkyl group, an acyloxyalkyl group, an alkenyl group, or an aryl group; and $Z^1$ and $Z^2$ are the same or different and each represents the nonmetallic atoms necessary to complete a heterocyclic nucleus; and 3. a barrier composition separating said enzyme and said dye and having a sample intercept area that is at least coextensive with said enzyme sample intercept area, said composition within its sample intercept area being uniformly permeable to said decomposition product and impermeable to interferants.

*51. In an integral element useful in the analysis of a fluid sample for a predetermined analyte, the element including*

*1. a reagent capable of producing ammonia vapor from the fluid sample; and*

*2. a reagent capable of interacting with said ammonia to provide a detectable change;*

*the improvement comprising*

*a barrier composition separating substantially all of said reagent (1) from said reagent (2), said barrier composition being substantially uniformly permeable to said ammonia and substantially impermeable to interferants.*

*52. An element as defined in claim 51, wherein said reagent (2) is a leuco dye selected from the group consisting of leuco cyanine dyes, nitro-substituted leuco dyes, and leuco phthalein dyes.*

* * * * *

UNITED STATES PATENT AND TRADEMARK OFFICE

CERTIFICATE OF CORRECTION

PATENT NO. Re. 30,267

DATED May 6, 1980

INVENTOR(S) Barbara J. Bruschi

It is certified that error appears in the above-identified patent and that said Letters Patent are hereby corrected as shown below Col. 14, line 37, "—C=" should read ---—CH= --.

Col. 16, line 12, "nitrobenaoxazole", should read --nitrobenzoxazole--; line 57, "pyrolo", should read --pyrrolo--.

Col. 17, line 54, that part of the formula reading "C-CH=(CH-CH$_n$)CH-", should read -- C-CH(CH-CH)$_n$=CH- --.

Col. 19, line 49, after "has", insert --a value of 5.--; line 54, before "$X^{1-}$", insert --6.--.

Col. 22, line 55, "Hydolysis", should read --Hydrolysis--.

Col. 23, line 37, that part of the structure reading "N-CH$_2$,", should read -- N-CH$_3$, --.

Col. 24, line 19, "pryzbylowicz", should read --Przybylowicz--.

Col. 30, line 53, "transmited", should read --transmitted--.

Col. 31, line 41, after "represents" insert --1--.

UNITED STATES PATENT AND TRADEMARK OFFICE

CERTIFICATE OF CORRECTION

PATENT NO. Re. 30,267

DATED May 6, 1980

INVENTOR(S) Barbara J. Bruschi

It is certified that error appears in the above-identified patent and that said Letters Patent are hereby corrected as shown below Col. 35, line 61, that part of the formula reading "$(A=(L-L)_m=C-CH_2-(CH=CH)_2-$", should read -- $A\{L-L\}_m=C-CH_2\{CH=CH\}_k$ --.

Signed and Sealed this

Seventeenth Day of February 1981

[SEAL]

Attest:

RENE D. TEGTMEYER

Attesting Officer

Acting Commissioner of Patents and Trademarks